US011302422B2

(12) United States Patent
Califano et al.

(10) Patent No.: US 11,302,422 B2
(45) Date of Patent: Apr. 12, 2022

(54) METHODS AND SYSTEMS FOR IDENTIFYING A DRUG MECHANISM OF ACTION USING NETWORK DYSREGULATION

(71) Applicant: THE TRUSTEES OF COLUMBIA UNIVERSITY IN THE CITY OF NEW YORK, New York, NY (US)

(72) Inventors: Andrea Califano, New York, NY (US); Mukesh Bansal, New York, NY (US); Yishai Shimoni, New York, NY (US)

(73) Assignee: The Trustees of Columbia University in the City of New York, New York, NY (US)

( * ) Notice: Subject to any disclaimer, the term of this patent is extended or adjusted under 35 U.S.C. 154(b) by 708 days.

(21) Appl. No.: 15/305,006

(22) PCT Filed: May 11, 2015

(86) PCT No.: PCT/US2015/030118
§ 371 (c)(1),
(2) Date: Oct. 18, 2016

(87) PCT Pub. No.: WO2015/172135
PCT Pub. Date: Nov. 12, 2015

(65) Prior Publication Data
US 2017/0193199 A1 Jul. 6, 2017

Related U.S. Application Data

(60) Provisional application No. 61/991,005, filed on May 9, 2014, provisional application No. 62/027,045, filed on Jul. 21, 2014.

(51) Int. Cl.
| | |
|---|---|
| *G16C 20/10* | (2019.01) |
| *G16B 5/00* | (2019.01) |
| *G16B 35/00* | (2019.01) |
| *G16B 40/00* | (2019.01) |
| *G16C 20/60* | (2019.01) |
| *G16B 5/20* | (2019.01) |

(52) U.S. Cl.
CPC ............... *G16C 20/10* (2019.02); *G16B 5/00* (2019.02); *G16B 5/20* (2019.02); *G16B 35/00* (2019.02); *G16B 40/00* (2019.02); *G16C 20/60* (2019.02)

(58) Field of Classification Search
None
See application file for complete search history.

(56) References Cited

U.S. PATENT DOCUMENTS

| | | | | |
|---|---|---|---|---|
| 2003/0219764 A1* | 11/2003 | Imoto | ..................... | G16B 5/00 435/6.13 |
| 2006/0177827 A1 | 8/2006 | Dejori et al. | | |
| 2009/0063376 A1* | 3/2009 | Li | ........................... | G16B 5/00 706/13 |
| 2013/0183707 A1* | 7/2013 | Mangoubi | .............. | G16B 40/00 435/29 |

FOREIGN PATENT DOCUMENTS

WO   2004/094609 A2   11/2004

OTHER PUBLICATIONS

Gardner et al. (Science, vol. 301, No. 5629, pp. 102-105) (Year: 2003).*
Zhu et al. (PLoS Biology, Apr. 2012, vol. 10, Issue 4, e1001301, p. 1-19). (Year: 2012).*
Schadt et al. (Nature Reviews Drug Discovery, 2009, vol. 8, pp. 286-295), (Year: 2009).*
Bansal, M., et al, "Inference of Gene Regulatory Networks and Compound Mode of Action From Time Course Gene Expression Profiles," Bioinformatics 22(7):815-822, Jan. 17, 2006.
Gardner, T.S., et al., "Inferring Genetic Networks and Identifying Compound Mode of Action via Expression Profiling," Science 301(5629):102-105, Jul. 4, 2003.
Iorio, F., et al., "Discovery of Drug Mode of Action and Drug Repositioning From Transcriptional Responses," Proceedings of the National Academy of Sciences 107(33):14621-14626, Aug. 17, 2010.
Lamb, J., et al., "The Connectivity Map: Using Gene-Expression Signatures to Connect Small Molecules, Genes, and Disease," Science 313(5795):1929-1935, Sep. 29, 2006.
Extended European Search Report dated Jan. 9, 2019, in European Patent Application No. 15789337.1, filed May 11, 2015, 4 pages.
International Search Report and Written Opinion dated Oct. 19, 2015 in International Application No. PCT/US15/30118.
Zhu et al., "Stitching together Multiple Data Dimensions Reveals Interacting Metabolomic and Transcriptomic Networks That Modulate Cell Regulation," PLoS Biol 10(4):e1001301 (2012).

* cited by examiner

*Primary Examiner* — Pablo S Whaley
(74) *Attorney, Agent, or Firm* — Barry L. Davison; Davis Wright Tremaine LLP

(57) ABSTRACT

Techniques to identify a mechanism of action of a compound using network dysregulation are disclosed herein. An example method can include selecting at least a first interaction involving at least a first gene, determining a first n-dimensional probability density of gene expression levels for the first gene and one or more genes in a control state, determining a second n-dimensional probability density of gene expression levels for the first gene and one or more genes following treatment using at least one compound, estimating changes between the first probability density and the second probability density, and determining whether the estimated changes are statistically significant.

11 Claims, 22 Drawing Sheets

Specification includes a Sequence Listing.

METHODS AND SYSTEMS FOR IDENTIFYING A DRUG MECHANISM OF ACTION USING NETWORK DYSREGULATION

CROSS-REFERENCE TO RELATED APPLICATIONS

This application is a U.S. National Stage Patent Application under 35 U.S.C. § 371 of International Application No. PCT/US2015/030118, filed on May 11, 2015, which claims priority to U.S. Provisional Application Ser. No. 61/991,005, filed on May 9, 2014, and 62/027,045, filed on Jul. 21, 2014, the contents of each of which are incorporated by reference herein in their entirety.

The content of the text file named "2022-01-03 0105272-003USO Sequence Listing.txt," which was created on Jan. 3, 2022, and is 5 KB in size, is hereby incorporated by reference in its entirety.

STATEMENT REGARDING FEDERALLY SPONSORED RESEARCH

This invention was made with government support under Grant Nos. U01 CA 164184, U01 HL 111566, and U54 CA 121852, each awarded by the National Institute of Health (NIH). The government has certain rights in the invention.

BACKGROUND

The mechanism of action (MoA) of a compound can be defined as the set of biochemical interactors and effectors through which it produces its pharmacological effects, which are often cell-context specific. A MoA can be used for the development of new drugs, understanding their side effects, and drug repositioning. However, such identification can be challenging, expensive, and require large experimental setups.

Such challenges are only partially addressed by certain experimental and computational strategies. Many experimental approaches rely on direct binding assays, such as affinity purification or affinity chromatography assays. These methods can be generally limited to the identification of high-affinity binding targets, rather than the full protein repertoire responsible for compound activity in a tissue. As a result, these methods can miss certain indirect effectors, as well as low-affinity binding targets that can either have desirable pharmacological properties or drive undesired side effects. For instance, protein kinase inhibitors can be screened against all kinases, but can miss other relevant targets, as shown by the reclassification of the MET tyrosine receptor kinase inhibitor tivantinib as a microtubule inhibitor. In addition, certain approaches are only amenable to in vitro studies and can miss complex effects resulting from paracrine, endocrine, and contact signals in vivo, and in specific tissue contexts.

Although chemo-informatics methods have also been developed, certain techniques assess MoA similarity or specific small-molecule/target interactions by leveraging the integration of structural and genomic information, text-mining algorithms, or machine learning methods for data-mining. As such, they can rely on detailed three-dimensional structures of both the drug molecules and the target proteins or on prior knowledge (literature or database derived) of related MoA compounds.

Techniques based on systematic gene expression profiling (GEP) following compound perturbations in cell lines have also been developed in connection with computational methods for MoA analysis. These can range from simple functional gene characterization based on differential expression analysis to comparing novel compounds of unknown MoA to large reference compendia of perturbational GEPs. The latter can use a variety of similarity metrics to assess the similarity of GEPs representing the response of disease-related cell lines to perturbation by compounds with established MoA or to RNAi-mediated gene silencing assays. However, certain methods are mostly comparative in nature and thus poorly suited to de novo MoA elucidation or to recognize subtle MoA differences, leading for instance to undesired toxicity.

Another option is network-based methods which, rather than focus on the characteristics of individual genes, estimate changes in gene-product activity by integrating expression over its interacting partners or pathways. This can allow using context specific knowledge and molecular interaction data while also providing robustness by integrating signals over multiple genes. However, certain methods either rely on prior knowledge of pathways mediating compound activity, making them unsuitable for genome-wide analyses, or require very large samples sizes (n>100), thus making them impractical even for small compound libraries.

Accordingly, there is a need to develop improved methods for identifying the mechanism of action of compounds.

SUMMARY

The presently disclosed subject matter provides methods and systems for identifying a mechanism of action for a compound.

According to one aspect of the disclosed subject matter, methods for identifying a mechanism of action of a compound using network dysregulation are provided. In an exemplary embodiment, the method can include selecting at least a first interaction involving at least a first gene and determining, e.g., using a processing arrangement, a first n-dimensional probability density of gene expression levels for the first gene and one or more genes in a control state. In some embodiments, n can be equal to two; one or more genes can be one gene. The method can also include determining a second n-dimensional probability density of gene expression levels for the first gene and one or more genes following treatment using at least one compound and estimating changes between the first probability density and the second probability density. In some embodiments, estimating can include using a Kullback-Leibler divergence.

The method can further include determining whether the estimated changes are statistically significant. In some embodiments, this feature can include a null distribution generated by $10^5$ Kullback-Leibler divergence values estimated from random pairs of genes (regardless of whether the genes share a network edge), providing a P-value for the dysregulation of each edge in the network. In some embodiments, the estimating can include estimating on an interaction by interaction basis.

In some embodiments, selecting a first interaction can include selecting m interactions, and repeating the process for each of the m interactions. For example, the m interactions can be every interaction ending in the first gene in a regulatory network. The method can include determining whether each interaction is dysregulated if the estimated changes are statistically significant. The method can include determining whether the first gene is dysregulated based at least in part on the significance of each interaction. In some embodiments, determining whether the first gene is dysregulated can be based at least in part on an integration of the significance of each interaction. In some embodiments, the integration of the significance can include estimating the residual of a linear fit to the first gene and using the covariance matrix of the resulting residuals as an input to Brown's method.

The first gene can include a plurality of genes, and the method can include repeating the process for a plurality of genes. In some embodiments, the method can include identifying a mechanism of action of the compound by selecting genes that are determined to be significant. The compound can include a plurality of compounds, and the method can include repeating processing for each of the plurality of compounds, and identifying two or more compounds with similar pharmacological effect.

In another exemplary embodiment of the disclosed subject matter, methods to identify compounds with similar pharmacological effect is provided. An example method can include selecting a first interaction involving at least a first gene. The method can also include determining, e.g., using a processing arrangement, a first n-dimensional probability density of gene expression levels for the first gene and one or more genes in a control state. In some embodiments, n can be equal to two; one or more genes can be one gene.

The method can include determining a second n-dimensional probability density of gene expression levels for the first gene and one or more genes following a first compound treatment using a first compound and estimating changes between the first probability density and the second probability density. The method can further include determining whether the estimated changes are statistically significant, and determining whether the interaction is dysregulated if the estimated changes are statistically significant.

The method can be repeated for each of m interactions, wherein the m interactions include every interaction ending in the first gene in a regulatory network. The method can include determining whether the first gene is dysregulated based at least in part on the significance of each interaction. In some embodiments, determining whether the first gene is dysregulated can be based at least in part on an integration of the significance of each interaction. In some embodiments, the integration of the significance can include estimating the residual of a linear fit to the first gene and using the covariance matrix of the resulting residuals as an input to Brown's method.

The method can be repeated for a plurality of genes, and a mechanism of action of the first compound identified by selecting genes that are dysregulated. The method can also be repeated for a plurality of compound treatments using a plurality of compounds. Further, the method can include identifying two or more compounds with similar pharmacological effect. In some embodiments, identifying two or more compounds with similar pharmacological effect can include predicting that two or more compounds share similar pharmacological effect based at least in part on the significance of the similarity between their predicted mechanisms of action. In some embodiments, estimating can include using a Kullback-Leibler divergence. In some embodiments, estimating can include estimating on an interaction by interaction basis.

The description herein merely illustrates the principles of the disclosed subject matter. Various modifications and alterations to the described embodiments will be apparent to those skilled in the art in view of the teachings herein. Accordingly, the disclosure herein is intended to be illustrative, but not limiting, of the scope of the disclosed subject matter.

DETAILED DESCRIPTION

The methods and systems presented herein can be used for identifying a mechanism of action for a compound and identifying compounds with similar pharmacological effect. The disclosed subject matter can identify relevant MoA proteins by assessing the global dysregulation of their molecular interaction repertoire, following compound perturbation, using regulatory networks. The disclosed subject matter will be explained in connection with an example method referred to herein as Detecting Mechanism of Action by Network Dysregulation (hereinafter "DeMAND") to elucidate compound MoA by interrogating tissue-specific regulatory networks using small-size gene expression profiling (GEP) datasets (e.g., n≥6 samples) representing in vitro or in vivo, compound-specific perturbation.

Figure 1:
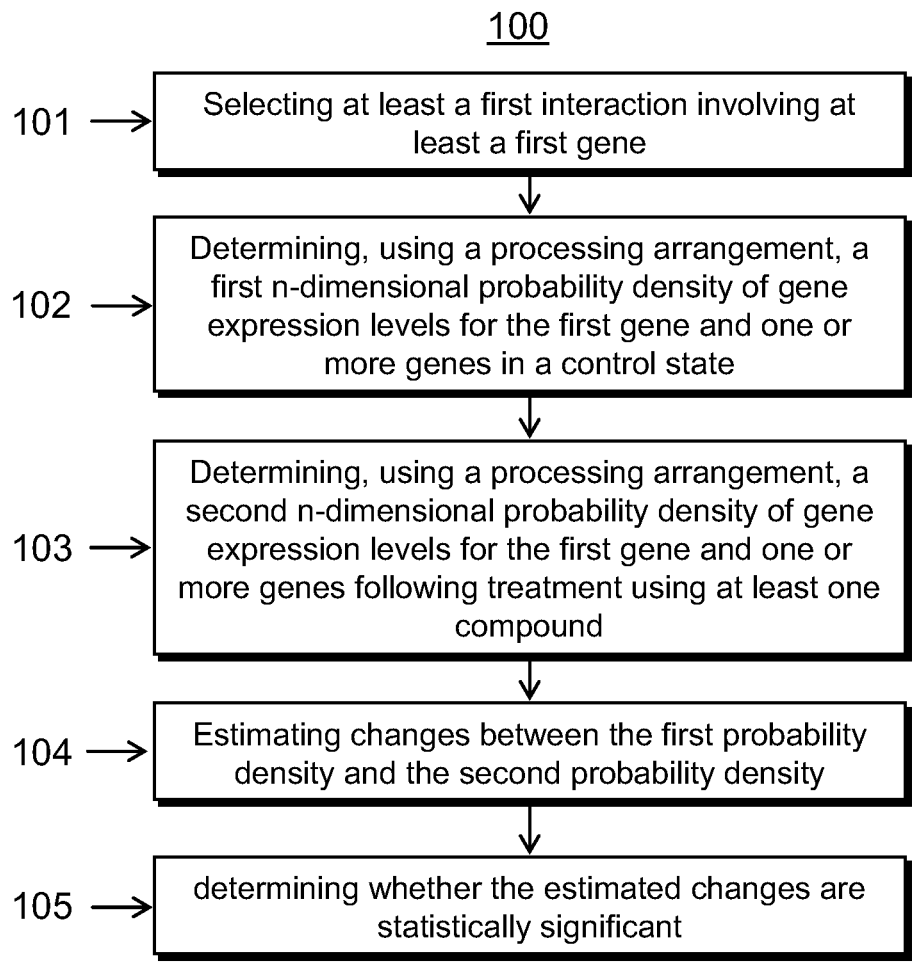
FIG. 1 illustrates a method for identifying a mechanism of action of a compound using network dysregulation.

FIG. 1 shows, for the purpose of illustration and not limitation, a method (100) for identifying a mechanism of action of a compound using network dysregulation. The method can include selecting at least a first interaction involving at least a first gene (101). At (102), the method includes determining, using a processing arrangement, a first n-dimensional probability density of gene expression levels for the first gene and one or more genes in a control state. In some embodiments, n can be 2, and one or more genes can be one gene. At (103), the method includes determining, using a processing arrangement, a second n-dimensional probability density of gene expression levels for the first gene and one or more genes following treatment using at least one compound. At (104) the method can include estimating changes between the first probability density and the second probability density. In some embodiments, estimating can be performed on an interaction by interaction basis. Estimating can use a Kullback-Leibler divergence (described in greater detail below). At (105) the method can include determining whether the estimated changes are statistically significant. For example, whether the estimated changes are statistically significant can be determined as described in greater detail below. In some embodiments, the method can include using a null distribution generated by $10^5$ Kullback-Leibler values estimated from random pairs of genes, and providing a P-value for the dysregulation of each edge in the network.

Figure 2:
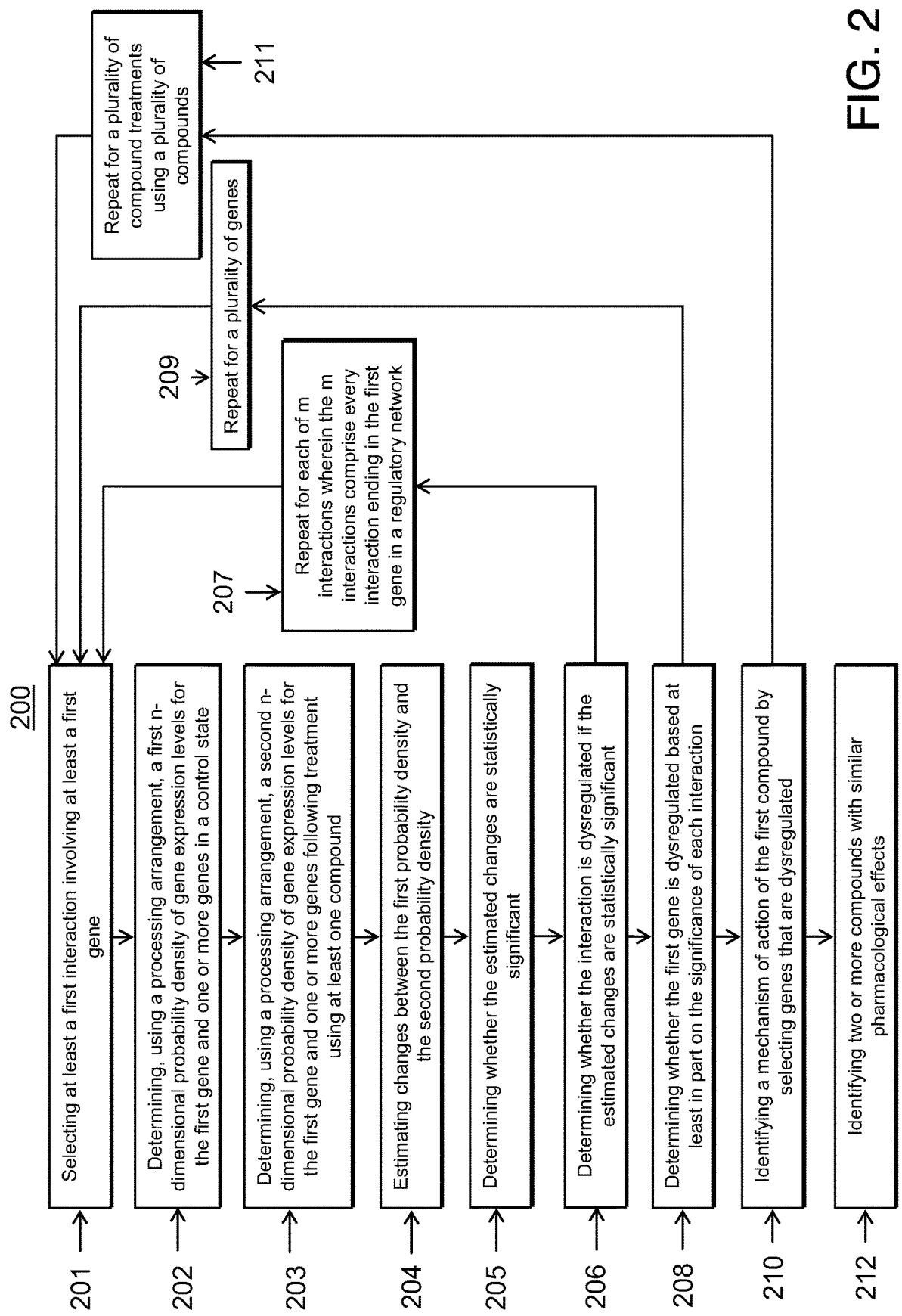
FIG. 2 illustrates a method for identifying compounds with similar pharmacological effect.

FIG. 2 shows, for the purpose of illustration and not limitation, a method for identifying compounds with similar pharmacological effect. At (201) the method can include selecting at least a first interaction involving at least a first gene. At (202) the method can include determining, using a processing arrangement, a first n-dimensional probability density of gene expression levels for the first gene and one or more genes in a control state. At (203) the method can include determining, using a processing arrangement, a second n-dimensional probability density of gene expression levels for the first gene and one or more genes following treatment using at least one compound. At (204) the method can include estimating changes between the first probability density and the second probability density. For example, estimating can be performed on an interaction by interaction basis and can use a Kullback-Leibler divergence. At (205) the method can include determining whether the estimated changes are statistically significant. At (206) the method can include determining whether the interaction is dysregulated if the estimated changes are statistically significant. At (207) the method can be repeated for each of m interactions. The m interactions can include every interaction ending in the first gene in a regulatory network. At (208) the method can include determining whether the first gene is dysregulated based at least in part on the significance of each interaction. At (209) the method can be repeated for a plurality of genes. At (210) the method can include identifying a mechanism of action of the first compound by selecting genes that are dysregulated. At (211) the method can be repeated for a plurality of compound treatments using a plurality of compounds. At (212) the method can include identifying two or more compounds with similar pharmacological effects.

Example: DeMAND

Given the potential (G ↔ G') interactions of a candidate gene-product G (i.e., its regulon) including transcriptional, signaling, and protein-complex related ones, if G belongs to a compound's MoA, then it can be assumed that its regulon will be dysregulated by the compound's activity. Thus, such dysregulation can be assessed by measuring the change in the joint probability density of the gene expression p(G, G'), across the pairwise regulon interactions. This can capture direct compound effects on the candidate MoA gene expression and modulation of the interacting partner's expression via either direct or indirect regulatory mechanisms (e.g., feedback loops).

For example, consider a candidate MoA gene product G regulating a set of transcriptional targets. A targeted inhibitor will significantly alter the joint expression probability density of G and its targets, as the expression of the latter will be affected while the expression of G is generally unaffected. Thus, significant change in the interactions probability density p ($G, G_i$) can be observed following compound perturbation, as illustrated by the probability density of 3 dysregulated interactions in FIG. 3 and in the experimental procedures discussion below.

The Kullback-Leibler divergence (KLD) can provide an established and effective metric to quantitatively assess changes in the probability density of one or more variables. The KLD can assess the loss of information when one probability density is used as an approximation of the other, and can therefore be interpreted in an information-theoretic context. Thus, for each candidate dysregulated interaction (G ↔ G'), the statistical significance of the KLD of the probability density p (G, G'), for each G' gene in its regulon, can be estimated before and after compound perturbation. The statistical significance of the individual KLD analyses can then be integrated across the regulon interactions, producing a global statistical assessment of the compound-mediated dysregulation of G. To avoid overestimating such integrative significance, due to interaction dependencies, a modification of Brown's method that compensates for the integration of correlated evidence can be used. Candidate MoA genes are then ranked based on their global statistics.

To identify the regulon of each gene-product of interest, a set of established network reverse engineering algorithms described below can be used. However, the disclosed subject matter does not require such algorithms, and rather can use networks generated by alternative techniques, both computational and experimental.

The accuracy of DeMAND-inferred MoA genes for 14 selected compounds, in a perturbation dataset (DP14) was evaluated. This includes 276 GEPs of diffuse large B-cell lymphoma cells (OCI-LY3), following perturbation with 14 distinct compounds (of which 11 have established primary targets, see experimental procedures, and DMSO as control media, at two concentrations and three time points, in triplicate. The network for these analyses was produced using a dataset of 226 U133p2 GEPs representing both normal and tumor related human B-cells (see experimental procedures). Although DeMAND can predict both compound targets (i.e., high-affinity binding proteins) and effectors/modulators, its performance was illustratively systematically benchmarked against the former.

In this analysis, DeMAND identified the primary targets of 7 of the 11 tested compounds as statistically significant (at a False Discovery Rate, FDR≤0.1) (see below and FIG. 4A). Since the GEPs used in this analysis were obtained at multiple time points (6, 12 and 24 hours), an assessment was made regarding whether analyses at individual time points can be more informative than integration across multiple (e.g., all) time points. Several established targets can be predicted at high specificity only at some of the time points (FIG. 4B), consistent with expectations that compound activity can be mediated over different time scales. Yet, integrative analysis over multiple (e.g., all) time points performed as well or better than that of the individual time point for all but for 2 compounds (monastrol and doxorubicin). For these, the direct target was significant only when GEPs at specific time points were used. In total, primary targets for 9 of the 11 compounds were elucidated either from the multi-point analysis or from the single point analysis.

DeMAND's performance on primary target inference was compared with that of differential expression analysis, by t-test statistics. DeMAND predictions systematically outperformed t-test analyses, except for blebbistatin for which neither method identified the primary target (myosin II) as statistically significant (FIG. 4A). When the fraction of direct targets identified by the two methods in their top predictions (sensitivity) was compared as shown in FIG. 5A, DeMAND had an almost 5-fold better sensitivity in predicting established compound-targets among the top 100 predictions, compared to t-test analysis (15% vs. 3%), which was highly statistically significant (p=$5\times10^{-4}$, and p=0.06 by $\chi^2$ test, respectively). Furthermore, significant targets identified by differential expression analysis were also significant by DeMAND analysis, but not the opposite. Overall, considering the complete area under the receiver operator characteristic (ROC) curve (AUC), which is a threshold free metric designed to access a method's tradeoff between sensitivity and specificity in predicting direct target, DeMAND consistently outperformed the t-test, AUC=0.70 (p-value≤2×10$^{-16}$ by Fisher integration of individual Mann-Whitney p-values for each compound) vs. AUC=0.60 (p-value=3.5×10$^{-7}$), respectively, reflecting its significantly higher sensitivity, and specificity (FIG. 4C).

To further assess DeMAND's performance on MoA proteins that are not high-affinity compound targets, further analysis focused on two of the four compounds, camptothecin and doxorubicin, whose direct targets were missed by the analysis. Despite missing their primary targets, DeMAND effectively identified key MoA proteins for both these compounds. Specifically, Camptothecin (a TOP1 inhibitor) and doxorubicin (a TOP2A inhibitor) severely disrupt DNA repair and mitosis. DeMAND identified GADD45A, CDKN1A, PCNA, AURKA, PLK1, and CCNB1, which are downstream effectors of TOP1 and TOP2A inhibition, among the most statistically significant genes for these compounds (FIG. 5B), most of them in the top 20 for both compounds.

More specifically, GADD45A (growth arrest and DNA damage-inducible gene 45A), an established effector of DNA damage response, acts by forming protein complexes with CDKN1A (Cyclin-Dependent Kinase Inhibitor 1A), and PCNA (proliferating cell nuclear antigen), a processivity factor of DNA polymerase delta required for high-fidelity DNA replication and excision repair. In turn, if DNA damage is detected, CDKN1A, PCNA, and GADD45A regulate the activity of CCNB1 (cyclin B 1, a critical effector of the G2/M cell-cycle checkpoint), PLK1 (polo-like kinase 1), and AURKA (Aurora Kinase A, a mitosis regulator) either at the RNA or protein level. Of these six genes, only GADD45A and CDKN1A were differentially expressed, albeit at a much lower rank, following perturbation with these compounds. As a result, DeMAND identified key MoA proteins that were either undetectable or lower ranked by differential expression.

Detailed assessment of DeMAND-inferred proteins successfully highlighted key differences and commonalities in the MoA of compounds with similar primary targets that were undetectable at the gene expression level. For instance, camptothecin (TOP1), doxorubicin (TOP2A), and etoposide (TOP2A) are topoisomerase (TOP) inhibitors, leading to covalent trapping of the TOP-DNA cleavable complex and induction of single or double strand breaks. Consistently, DeMAND identified a common footprint in their inferred MoA, as shown above. However, it also identified specific effectors, such as KAT5/TIP60 (ranked 4$^{rd}$) for doxorubicin, suggesting potentially relevant differences from the other two TOP inhibitors, as shown in FIG. 5B. Indeed, contrary to etoposide and camptothecin, doxorubicin is also a strong DNA intercalator that induces histone release from open chromosomal sites (histone eviction), following large-scale KAT5-dependent histone acetylation, leading to cell cycle arrest. Again, differential expression did not identify the potential effectors of doxorubicin such as KAT5 and PCNA even in the top 1000 genes. The algorithm also identified SIK1 as a specific effector of doxorubicin (ranked 36$^{th}$). SIK1 is used for maintenance of cardiac progenitor cells (CPCs), thus pinpointing the compound's most prominent therapy-limiting adverse event, i.e., cardiomyopathy followed by congestive heart failure.

DeMAND can also successfully stratify compounds based on their common predicted MoA genes, emphasizing its specificity in predicting MoA of compounds. For instance, 5 of the 14 tested compounds were DNA damaging agents (i.e., camptothecin, doxorubicin, etoposide, mitomycin C, and vincristine). DeMAND predicted GADD45A, the canonical DNA-damage-inducible gene, as well as its well-known interactor genes, such as CDKN1, CCNB1 PCNA and AURKA [32-35] among the most statistically significant MoA-inferred genes for all of these compounds (FIG. 5C). Yet, the same genes were not significant for the compounds that did not induce DNA damage (FIG. 5C), suggesting that DeMAND can infer highly specific compound MoA proteins. In contrast, differential expression performed poorly and failed to identify most of these genes as statistically significant. Thus DeMAND can provide critical information to identify both "on-target" as well as potentially deleterious "off-target" effects of small molecule compounds.

To illustrate DeMAND is effective at elucidating novel MoA proteins, DeMAND-inferred MoA proteins can be for vincristine, an inhibitor of microtubule formation in mitotic spindle, and mitomycin C, an antineoplastic antibiotic. DeMAND successfully identified the known high-affinity target of vincristine (TUBB) as well as CCNB1, a known microtubule activity marker, among its top 5 predicted genes. The other 3 genes in the top 5 included VHL, RPS3A and NFKBIA. While two of these genes, RPS3A and VHL, are known to affect mitotic spindle assembly in human cell-lines, their function in mediating/modulating vincristine's activity is unknown.

Figure 6:
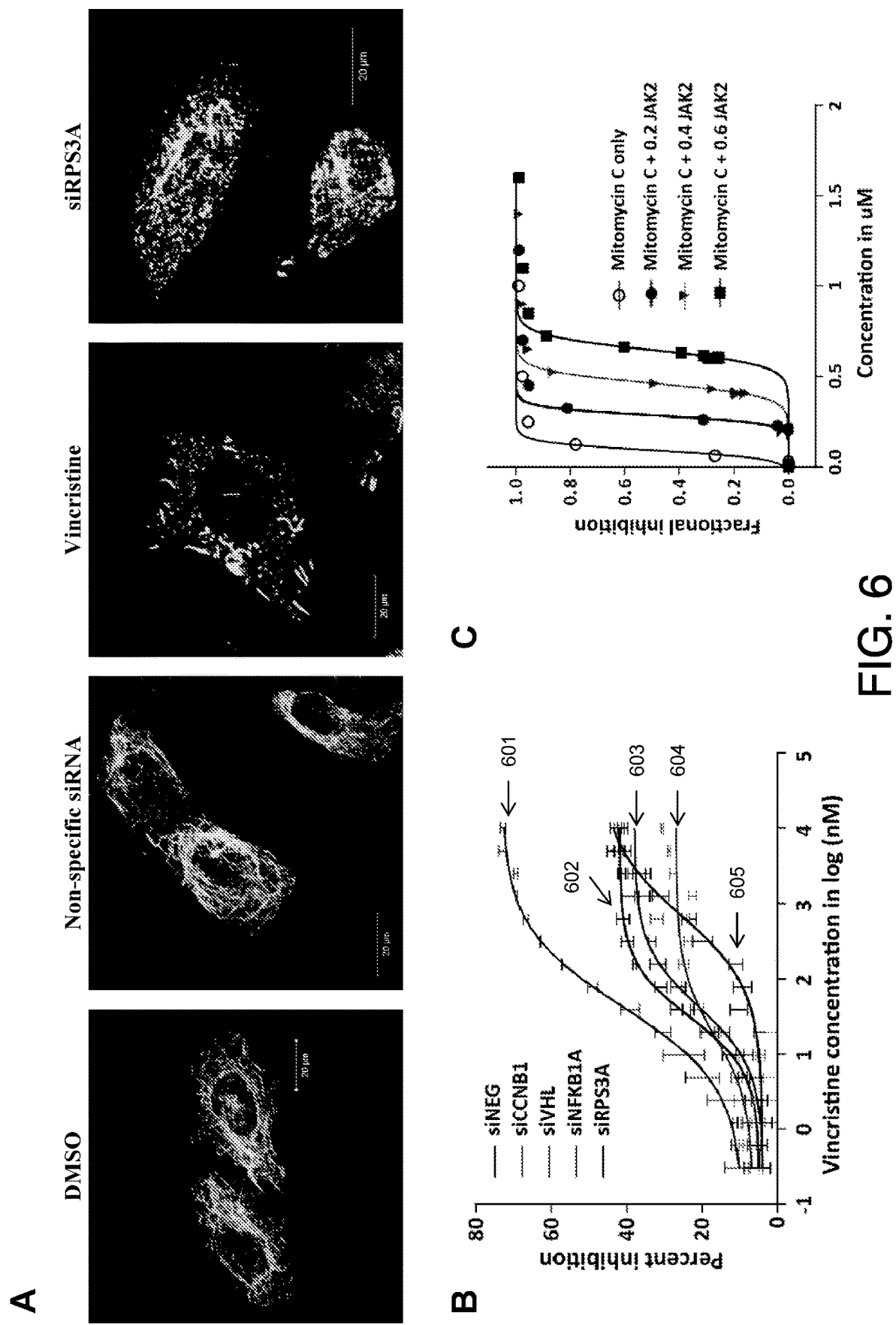
FIG. 6 illustrates experimental validation of predictions of dysregulation by vincristine and mitomycin C.

Probing the microtubule network with an anti-tubulin antibody, following silencing of these genes, confirmed that loss of RPS3A (but not of VHL, CCNB1 or NFKBIA) disrupts microtubules in adherent U-2-OS cells (FIG. 6A). Thus, to further validate the role of these genes in mediating vincristine's activity, dose-response curve assays in U-2-OS cells were performed, following siRNA-mediated silencing of each gene (see experimental procedures). These assays confirmed that all of these genes, except for NFKBIA, are key vincristine activity effectors and mediators. VHL silencing increased vincristine sensitivity by more than two-fold (FIG. 3B), while RPS3A and CCNB1 silencing had the opposite effect. Thus, 3 of top-5 DeMAND-inferred genes were experimentally validated as vincristine activity modulators, while a fourth one (TUBB) represents its primary target. In contrast, none of these genes were significantly differentially expressed and were thus undetectable by more traditional approaches. This suggests that, for some compounds, the false positive rate of the algorithm can be as low as 20%.

DeMAND also inferred the JAK2 kinase as an exclusive mitomycin C MoA protein (i.e., JAK2 was not significant by DeMAND analysis for other compound). This can be of importance since constitutive activity of JAK2 can cause chemo-resistance in lymphocytes, and in addition, recent studies suggest that constitutive JAK2 activity can control the outcome of DNA damage, repair and recombination events. Thus the effect of JAK2 inhibition on mitomycin C activity was tested, by measuring dose-response curves for this compound following treatment with varying amounts of the well-characterized JAK2 inhibitor TG101348 (FIG. 6C, see experimental procedures). The experiment revealed significant, dose-dependent antagonism between JAK2 inhibition and mitomycin C activity, thus confirming JAK2 as a key effector of mitomycin C activity.

Finally, DeMAND-inferred results for the antineoplastic and immune-modulating agent rapamycin were analyzed. While DeMAND could not predict the highest-affinity targets, MTOR and FKBP1A, many genes downstream of MTOR pathways were highly enriched in the top DeMAND-inferred genes (FIG. 4E, see experimental procedures), including many ribosomal genes. This is not a pleiotropic result, as the only other compound with significant enrichment for ribosomal genes was cycloheximide, which is also known to inhibit ribosomal activity, thus highlighting again the specificity of DeMAND predictions.

To assess the method's broad utilization potential, both its robustness and its data requirements were benchmarked. DeMAND's performance as a function of network accuracy and size, as well as of perturbation dataset size was evaluated. First, the results obtained were compared using an independent B-cell gene regulatory network, reconstructed from a distinct dataset of 254 Affymetrix U95av2 GEPs, as described below. For this comparison, the enrichment of statistically significant DeMAND-inferred genes (FDR≤0.1) was tested using the U95av2 network, against those inferred using the U133p2 network, by Gene Set Enrichment Analysis (GSEA). The analysis confirmed that DeMAND predictions were almost identical, independent of network model ($p<1\times10^{-9}$ by GSEA, FIG. 7A), confirming that DeMAND's performance is largely independent of specific profiling platforms and of the datasets used for network assembly. Further analysis showed that DeMAND predictions were virtually unaffected when up to 60% of network interactions were randomly removed (see FIG. 7B). Similarly, sub-sampling the GEPs showed that DeMAND predictions were virtually identical, when 6 or more samples representative of a compound's perturbation were used (FIG. 7C). Taken together, these data suggest that DeMAND is highly robust to network noise and especially to false negative interactions, and that it can be successfully applied to datasets as small as 6 treatment samples and 6 untreated controls.

Once the requirements for robust algorithm performance were objectively assessed, selected 13 additional datasets (GEO13) in the gene expression omnibus (GEO) database were selected, representing cell line GEPs following compound perturbation (Table 1). These sets were constrained to compounds with established primary targets for which a minimum of 6 profiles were available (for both compound-treated and control samples), and for which a context-specific regulatory network could be assembled. This included 7 human breast cancer and 6 human B-cell lymphoma perturbational datasets. Similar to the PD14 dataset, DeMAND identified one or more established direct targets as statistically significant for 62% of these compound perturbations (FDR≤0.1, FIG. 8A), while significantly outperforming t-test based method (AUC=0.82 vs. 0.74, respectively, p-value=$2.2\times10^{-16}$ vs. p-value=$5.9\times10^{-8}$, respectively, by Fisher integration of individual Mann-Whitney p-values for each compound) (FIG. 8B). Again, these differences were especially relevant among top predicted compounds, where DeMAND again achieved roughly 5-fold better performance than differential expression analysis (FIG. 8C).

TABLE 1

Table 1. 13 compound perturbation datasets from the GEO database

| Compound | Cellular context | GEO ID |
|---|---|---|
| Zoledronate | Metastatic breast cancer cell lines (MDA-MB-231) | GSE33552 |
| Valproic Acid | Chronic lymphocytic leukemia (Patient derived B cells) | GSE14973 |
| Genistein | Breast cancer cell lines (MCF-7) | GSE9936 |
| S-Equol | Breast cancer cell lines (MCF-7) | GSE9936 |
| Estradiol | Breast cancer cell lines (MCF-7) | GSE9936 |
| Rituximab | B-cell non-Hodgkin's lymphoma cell lines (K422) | GSE7292 |
| Thapsigargin | lytic-permissive lymphoblastoid cell lines | GSE31447 |

TABLE 1-continued

Table 1. 13 compound perturbation datasets from the GEO database

| Compound | Cellular context | GEO ID |
|---|---|---|
| Fluvastatin | Metastatic breast cancer cell lines (MDA-MB-231) | GSE33552 |
| MALT1 Inhibitor | Diffuse large B-cell lymphoma (Patient derived B cells) | GSE40003 |
| Docetaxel | Breast cancer cell lines (MCF-7) | GSE5149 |
| γ-Secretase Inhibitor | MCL cell lines | GSE34602 |
| Triptolide | Breast cancer cell lines (MCF-7) | GSE28662 |
| Actinomycin D | Breast cancer cell lines (MCF-7) | GSE28662 |

Having established DeMAND's performance in predicting MoA genes for reference compounds, the inferred MoA overlap of distinct compounds were predictive of their pharmacological similarity was examined. First, the statistical significance of the overlap of significant DeMAND-inferred MoA for the DP14 compound pairs (FDR≤0.1 by Fisher's Exact Test) was computed (see FIG. 9A). Among the 91 potential compound pairs, the six most similar ones included only topoisomerase inhibitors and other DNA-damaging agents (etoposide, doxorubicin, camptothecin, and mitomycin C). Thus, DeMAND successfully assessed high compound MoA similarity between topoisomerase inhibitors and other DNA-damaging agents even though it could not identify TOP1 or TOP2A among the inferred MoA genes. Accordingly, effector proteins can be as informative as direct targets in elucidating compound similarity.

To further evaluate this hypothesis, the method was applied to a much larger compound perturbation dataset (PD92), representing the gene expression profile of three distinct B-cell lymphoma cell lines (OCI-LY3, OCI-LY7 and U-2932), following perturbation with 92 unique FDA-approved, late-stage experimental, and tool compounds (see experimental procedures). Since only three GEPs per compound and cell lines are available in this dataset, it was used only to assess compound-pair similarity based on predicted MoA but not to predict primary compound targets (see experimental procedures).

DeMAND performance was objectively evaluated by comparing DeMAND-inferred similarity with objective similarity assessment, using the following three independent data sources: (a) compounds sharing established targets; (b) compounds sharing therapeutic and chemical characteristics, according to the Anatomical Therapeutic Chemical classification system (ATC) and (c) compounds with correlated drug-response profiles, as assessed by the Cancer Target Discovery and Development (CTD$^2$) consortium (see experimental procedures). The latter dataset recapitulates dose-response curve vectors representing 338 unique compounds profiled against 257 distinct cell lines, representing multiple tumor types. The fraction of validated similar pairs (precision) were evaluated based on each of the three evidence datasets, as a function of the number of significant pairs (precision curves, FIG. 9B). DeMAND-inferred pairs were highly enriched in pairs from three evidence datasets, as assessed by the evidences individually (i.e., p-value=$2\times10^{-8}$, $1.4\times10^{-5}$, and $9\times10^{-4}$, by GSEA, for pairs sharing the same ATC class, common established targets, and high dose-response vector correlation in the CTD2 dataset, respectively, FIG. 10A), and also when taken together (GSEA p-value=$7.6\times10^{-7}$). For instance, 8 of the top 10 and 43 of the top 100 DeMAND-inferred pair similarities were validated by at least one of the three datasets (p-value<2.2× $10^{-16}$ by Fisher exact test).

Figure 10A:
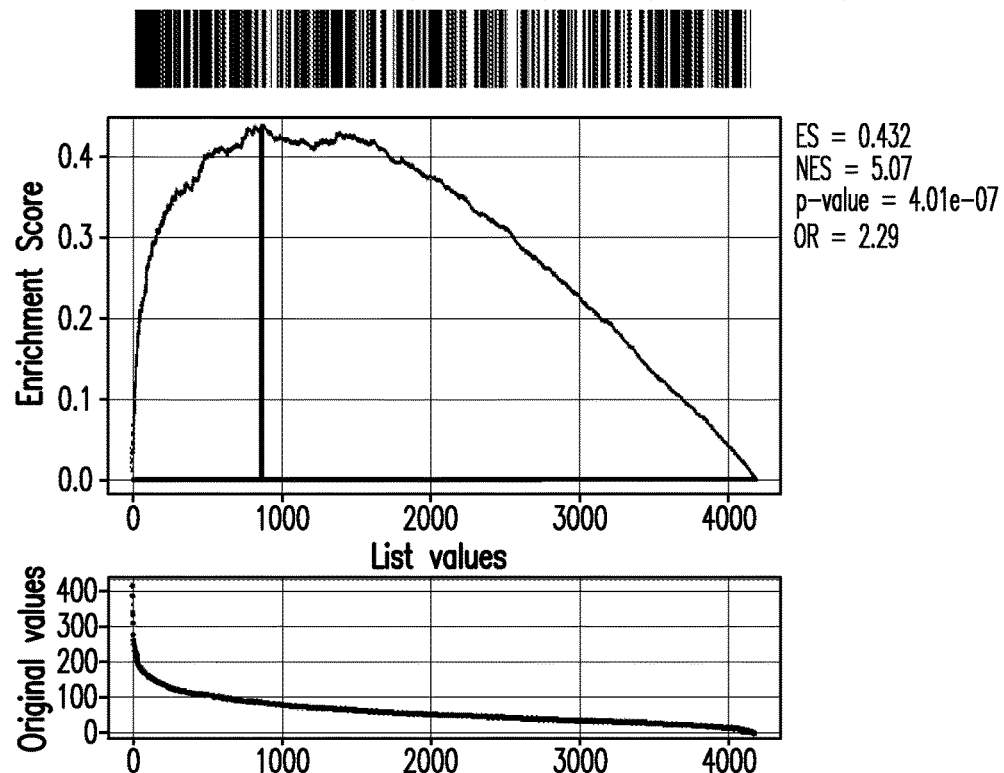
FIG. 10 illustrates performance analysis of compound similarity.
Figure 10B:
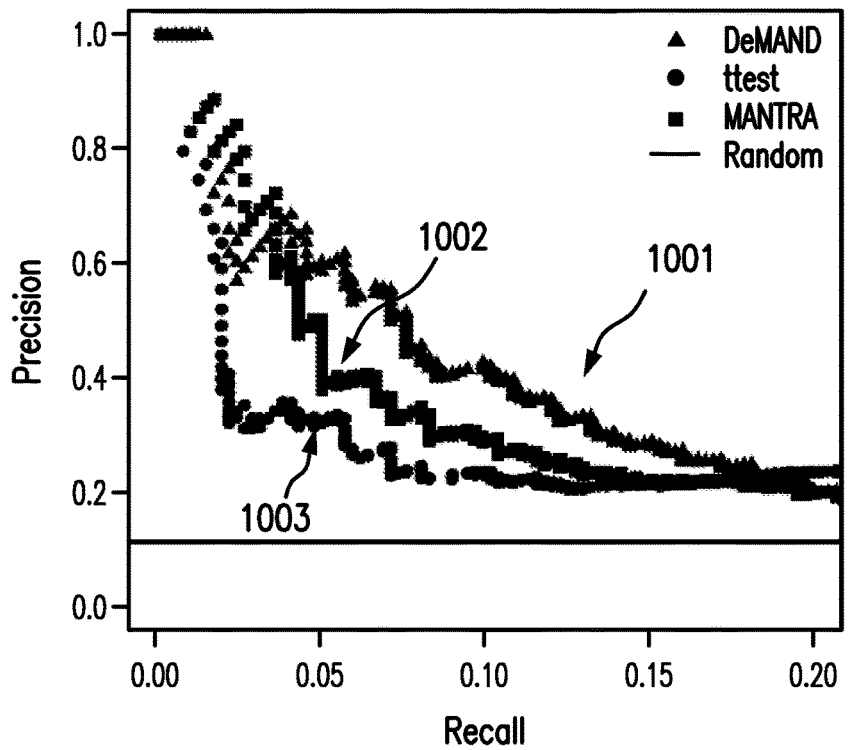

DeMAND outperformed predictions using similarity obtained by overlapping statistically significant differential expressed genes (e.g., by t-test statistics) by consistently achieving higher sensitivity at various precision values (FIG. 10B). DeMAND also outperformed another method, MANTRA, which uses mutual gene set enrichment analysis to compute similarity, again by achieving higher sensitivity at various desired precision values (FIG. 10B). Notably, while MANTRA can assess compound MoA similarity it was not designed to elucidate specific MoA genes. Thus, DeMAND outperformed MANTRA, even though it performed MoA similarity analysis using only a handful of genes predicted to be part of the compound MoA instead of the full gene expression signature. This further suggests that the MoA inferred by DeMAND are biologically and mechanistically relevant.

Figures 10C, 10D, 10E:
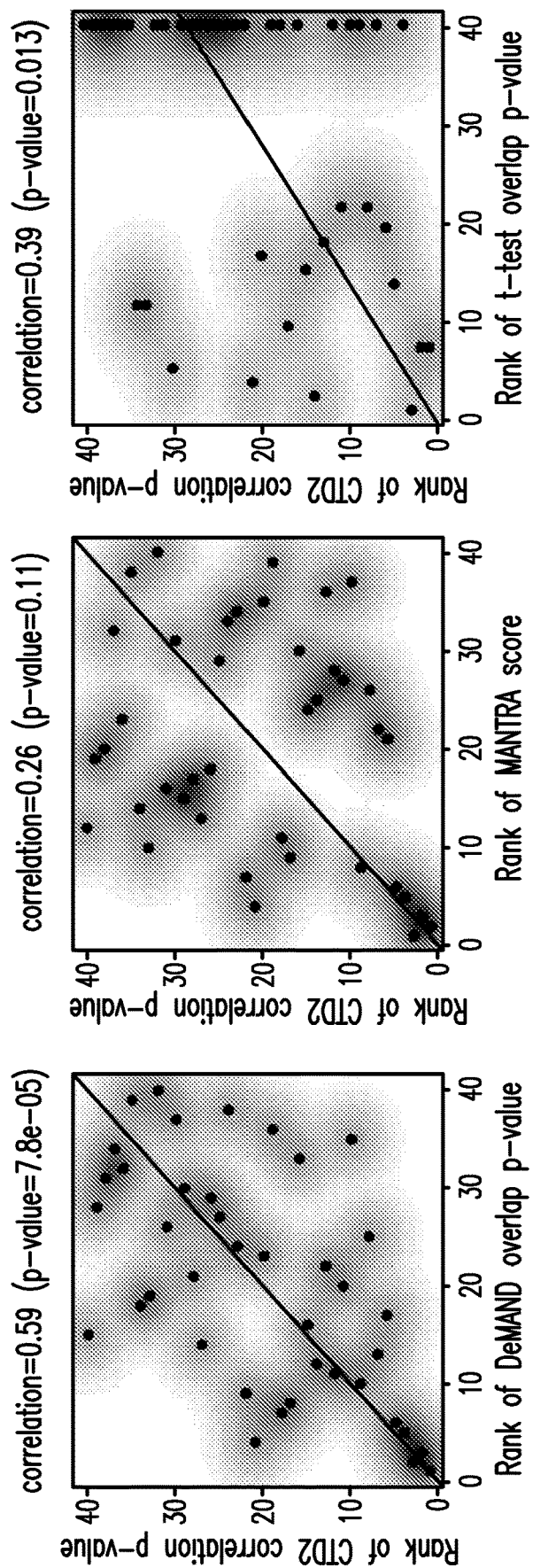

Finally, the correlation between compound-pair similarity as predicted by the methods and their $CTD^2$-based similarity was evaluated. DeMAND prediction achieved significant Spearman correlation (p=0.59, p-value=7.8×$10^{-5}$, FIG. 10C), while both the t-test and MANTRA methods did not achieve statistically significant correlation (FIGS. 10D, 10E). Thus, DeMAND can predict compounds with similar pharmacological effect and activity profile using only the GEP following their treatment in a single cell line.

To test whether two compounds with statistically significant DeMAND-inferred MoA similarity are likely to have common targets and effectors, altretamine and sulfasalazine were identified as the two compounds with the highest DeMAND-inferred MoA similarity (p-value=9.91×$10^{-81}$), among the pairs where the MoA of at least one compound was unknown. Altretamine is an FDA-approved antineoplastic drug with no known targets or effectors supporting its pharmacological effects. On the other hand, sulfasalazine can inhibit system $x_c^-$, the cystine-glutamate antiporter, thus preventing import of cystine into the cytoplasm and its reduction to cysteine. Since cysteine is a necessary metabolite in the biosynthesis of glutathione, sulfasalazine depletes cellular glutathione, thus inactivating enzymes that rely on reduced glutathione (GSH) as a cofactor, including glutathione peroxidase 4 (GPX4). This leads to toxic accumulation of lipid reactive oxygen species (ROS).

Figure 11:
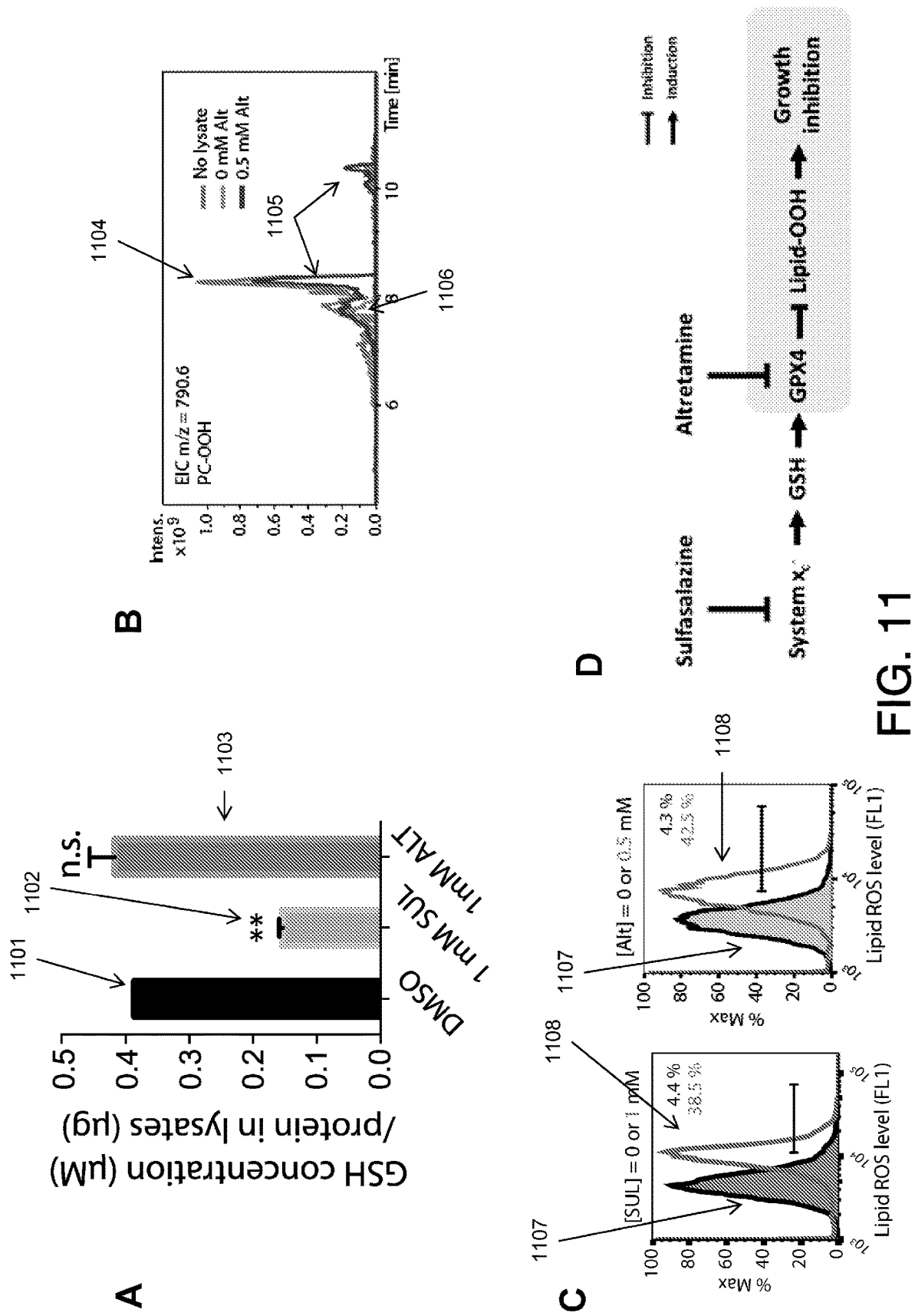
FIG. 11 illustrates that a disclosed embodiment identifies the MoA of altretamine.

Based on the inferred MoA similarity, whether altretamine can also modulate the system $x_c^-$-GPX4 pathway was tested. U-2932 cells were treated with altretamine and their GSH levels were assessed using Ellman's reagent (FIG. 11A). Sulfasalazine was used as a positive control for GSH depletion in U-2932 cells, confirming depletion of GSH levels following compound treatment. In contrast, altretamine did not deplete GSH levels, even after doubling its $IC_{50}$ at 24 hrs concentration, suggesting that the compound can target mechanisms downstream of GSH in this pathway. Thus U-2932 cells were treated with altretamine, and prepared cell lysates for an LC-MS based GPX4 assay. Phosphatidylcholine hydroperoxide (PC—OOH), a specific substrate for GPX4, was added to cell lysates and PC—OOH to PC—OH reduction was assessed by the mass chromatogram of the [PC—OOH+$H^+$] ion (m/z=790.5). As shown in FIG. 11B, lysates of untreated cells reduced PC—OOH levels completely, leaving no residual signal for the [PC—OOH+$H^+$] ion (m/z=790.5). In sharp contrast, lysates from altretamine treated cells displayed a significant [PC—OOH+$H^+$] signal, indicating that abrogation of PC-OOH reduction was mediated by GPX4 inhibition (experimental procedures). Indeed, since GPX4 is the only known enzyme capable of reducing lipid hydroperoxides, GPX4 inhibition is necessary to increases lipid-ROS levels. As expected, both sulfasalazine and altretamine were confirmed to induce lipid-ROS accumulation in U-2932 cells, as assessed by BODIPY-C11 staining and flow cytometry (see FIG. 11C and experimental procedures). Thus, DeMAND correctly predicted the unexpected and striking MoA similarity between two previously unrelated drugs, sulfasalazine and altretamine (see FIG. 11D). Moreover, these results suggest altretamine as a new inhibitor of GPX4 activity, and suggest that the antineoplastic activity of altretamine in patients can be due in part to inhibition of its enzymatic activity.

DeMAND elucidates compound MoA by assessing compound-mediated dysregulation of protein regulons on a genome-wide basis, using only gene expression data. DeMAND can reliably identify MoA related proteins and the latter can be effectively used to assess MoA and overall pharmacological effect similarity of arbitrary compound pairs. Indeed, using this approach one can identify and experimentally validate several genes previously unknown to be involved in the MoA of vincristine, mitomycin C, and altretamine. For altretamine one can also identify and validate a novel pharmacological effect of the drug (increased reactive oxidative stress leading to cell death).

Robustness analysis for DeMAND confirmed that its predictions are robust with respect to both gene expression and network variability, remaining virtually unchanged up to 60% degradation of network interactions. This can suggest resilience to false negative interactions in the network. Finally, unlike previous methods, DeMAND can be reliably used with very small perturbational GEP sets (i.e., containing as few as 6 control and 6 perturbation samples). This can allow application of the method to elucidating the MoA of relatively large compound sets, for instance to reveal potentially toxic off-target as well as novel on-target effectors and activity modulators. This can support application of the method to several large-scale repositories produced by efforts such as the Library of Integrated Network-Based Cellular Signatures (LINCS) dataset, representing GEPs following perturbation with ~4000 compounds. An additional advantage is the context-specific nature of the algorithm, which allows exploration of compound activity in specific cellular contexts of interest, including in vivo.

DeMAND leverages integration of GEPs obtained at multiple time points and at multiple compound concentrations, thus simplifying the experimental design, especially when the precise concentrations or time points at which the MoA can be revealed is unknown. Indeed, in the absence of specific knowledge, compound targets were optimally identified by integrating compound response at multiple time points, for all but two of the tested compounds. Yet, when available, knowledge of the specific compound activity timescale can also be helpful, as shown by identification of direct targets for two of the drugs that could not be elucidated by integrative analysis (FIG. 4B). Overall, the multipoint analysis can be chosen if the time-dependent response of the compound is unknown. However, comparison of multipoint and single point analyses can be used to provide further insight into compound MoA. For instance identification of the time-point most similar to the multipoint results can shed light on the compound activity timescale. Similarly, strong consistency of the analysis at two consecutive time points can suggest MoA proteins that can be missed by integrative analysis. The assays described herein have used sub-lethal compound concentrations to avoid contaminating the compound's MoA with mechanisms associated with downstream cell death mechanisms.

DeMAND predictions are highly specific, allowing classification of compounds into groups of similar function and identification of pathways that are relevant to compound MoA. For instance, for DNA-damaging compounds (camptothecin, doxorubicin, etoposide, vincristine and mitomycin C), DeMAND correctly predicted several of the hallmark genes involved in DNA-damage-induced response. The specificity was evidenced by the fact that relevant MoA proteins were inferred for DNA-damage inducing compounds and not for other compounds (including compounds exhibiting significant polypharmacology like H-7 dihydrochloride or cycloheximide).

In other examples, high compound-MoA specificity can be shown for doxorubicin, where DeMAND identified KAT5 as a key MoA-protein, in agreement with recent findings of doxorubicin-specific, KAT5-mediated histone eviction, as well as SIK1, a gene required for cardiac progenitor cells (CPCs) maintenance, providing a potential mechanistic link between doxorubicin and its known cardiac toxicity. SIK1 was also detected in the MoA of other DNA damaging agents, albeit at much lower rank/significance than doxorubicin, suggesting that these compounds should also be monitored for cardiac toxicity. In combinations, these findings confirm that DeMAND is not only effective in predicting direct compound targets but also key indirect effector proteins, thus allowing MoA inference and identification of potential effectors that can help elucidate both on-target pharmacology and off-target toxicity. Overall, DeMAND successfully identified both direct targets and indirect MoA-proteins for over 70% of tested compound. While experimental validation of vincristine specific novel MoA proteins suggests that actual false discover rate (FDR) can be as low as 20%, systematic FDR estimate can be difficult because compound MoA is very sparsely elucidated leading to significant FDR overestimates. For instance, before experimental validation, FDR for vincristine inferred MoA proteins was found to be 80%, with only TUBB was an established compound target/effector. However, systematic validation of the top 5 inferred MoA proteins revealed that FDR was not more than 20%.

DeMAND relies on the existence of high quality context-specific gene regulatory networks, which can represent a limitation for specific cellular contexts. However, given the abundance of data generated by large-scale projects such as the Cancer Genome Atlas (TCGA) and other related consortia, as well as the availability of increasingly accurate and comprehensive methods for context-specific network reverse engineering, this limitation is at best temporary. However, availability of cell-context-specific regulatory networks does not guarantee identification of MoA proteins that are poorly represented in the network. This can happen, for instance, because expression of individual genes can be poorly assessed by specific platforms or because of false positives introduced by reverse engineering methods. For instance, for blebbistatin (a myosin II inhibitor), using the U95av2 network, DeMAND identified PTK2B, GRB2 and FYN, all of which are both direct regulators of myosin II phosphorylation, and responders to myosin II perturbation (see FIG. 4D). Yet, due to lack of GRB2 representation in the U133p2 network, this gene could not be inferred when the U133p2 network was used. It is also important to highlight that DeMAND analysis of the DP14 and DP92 datasets, using a high quality context-free network from the STRING database, was still able to identify ubiquitous targets and effectors (e.g., those involved in cell cycle and DNA damage repair mechanisms) with high precision and sensitivity, but exhibited lower performance both in compound similarity analysis and in the identification of genes with context specific function/expression. This suggests that non-context-specific networks can still be used for DeMAND analyses, albeit with an increase in false positive and negative predictions. This is likely to include genes representing compound specific differences and potential toxicity related effectors, which are optimally highlighted only when using context specific networks.

Experimental Procedures

DP14 dataset: This dataset contains GEPs of OCI-LY3 cell line (a human diffuse large B-cell lymphoma cell line) treated with 14 distinct individual compounds and profiled at 6 hrs, 12 hrs, and 24 hrs following compound treatment, all in triplicate. For treatment, two different concentrations of the compounds corresponding to IC20 at 24 hrs and IC20 at 48 hrs were used. GEP of DMSO treated samples and profiled at the three different time points, in octuplicate were used as control, resulting in a total of 276 GEPs (FIG. 5A) from this dataset.

GEODB: This dataset contains GEP of 13 different compounds, obtained from 9 independent expression sets obtained from the Gene Expression Omnibus (GEO) (Table 1). Each expression set had at least 6 DMSO controls and 6 samples for compound treatment. Three of the expression sets were profiled on MCF7 breast cancer cell lines (GSE9936-3 compounds, GSE5149, and GSE28662-2 compounds), and two on MDA-MB-231 metastatic breast cancer lines (GSE33552-2 compounds). The rest of the expression sets were profiled in a B-cell lymphoma cell lines, which are chronic lymphocytic leukemia patient derived cell lines (GSE14973), K422 non-Hodgkin's lymphoma cell lines (GSE7292), lytic-permissive lymphoblastoid cell lines (GSE31447), diffuse large B-cell lymphoma patient derived cell lines (GSE40003), and mantle cell lymphoma cell lines (GSE34602).

DP92: This dataset contains GEPs of 92 distinct FDA-approved, late-stage experimental, and tool compounds in 3 different B-cell lymphoma cell lines (OCI-LY3, OCI-LY7 and U-2932), profiled at 6, 12, and 24 hrs following compound treatment. The compounds were treated using $IC_{20}$ at 24 hrs concentration. DMSO was used as control media at each of the 3 time-points, resulting in a total of 857 GEPs.

To run DeMAND, context specific gene-regulatory networks including both protein-DNA interactions and protein-protein interactions were generated (see Table 2). The context specific information for these networks was obtained from GEPs derived from the same context whereas context independent information is obtained from large number of experimental and computational evidences. Finally, Naïve Bayes Classifier was used to integrate various evidences for an interaction to obtain final interactome. A detailed description on how to generate interactome is provided below. To generate U133p2 human B-cell interactome 226 GEPs were used, whereas for U95av2 human B-cell interactome 254 GEPs were used. To generate the breast cancer interactome (BCI) GEPs obtained from CMAP2 dataset were used. This dataset contains 3,115 profiles for MCF7 cell line. Many of these profiles in this dataset show no response to the treatment, thus causing high redundancy. To reduce this redundancy, a background variability distribution of number of genes with greater than 2 fold change was created by randomly comparing 2 control (DMSO) samples. Then for each treatment, a sample is filtered out if number of genes showing at least a 2 fold change difference when compared with the corresponding control sample from the same batch is less than the threshold determined from the background distribution. This leads to the selection of 448 samples that were finally used to generate BCI.

TABLE 2

Table 2: Networks;

| Network | Cellular context | Number of interactions | Number of PDI* | Number of PPI** | Source data |
|---|---|---|---|---|---|
| Bcell-U95av2 | B cell lymphoma | 63,536 | 41,727 | 22,554 | 254 B cell lymphoma gene expression profiles |
| Bcell-U133p2 | B cell lymphoma | 142,416 | 113,843 | 28,573 | 226 B cell lymphoma gene expression profiles |
| BRCA-MCF7 | Breast cancer | 124,898 | 26,259 | 98,639 | 448 breast cancer gene expression profiles |
| STRING | . | 79,160 | . | 79,160 | Experimentally validated protein-protein interactions |

*PDI: Transciption Factor (protein) - target (NDA) interaction;
**PPI: protein - Protein interaction For the pairs of genes connected by an interaction in the network, their expression in a given condition (treatment or control) is transformed into a two-dimensional probability density. To allow for non-linearity, expression data was rank-transformed by taking compound perturbation and control samples together, for the genes. The probability density is estimated using Gaussian kernel smoothing, by replacing the points with a two-dimensional Gaussian probability density centered on that point using Silverman's approach. The sum of the Gaussian probabilities densities from the points corresponding to compound perturbation provides the perturbation probability density P, while the sum of the Gaussian distributions from the points corresponding to control samples provides the control probability distribution Q. The distributions are evaluated at each integer grid point in the rank space defined by the number of samples, and normalized to a sum of 1 to create a valid discrete probability distribution.

The distance between the two discrete probability distributions is evaluated using the Kullback-Leibler divergence (KLD), defined as $$KLD(P|Q) = \Sigma_i P_i \log\left(\frac{P_i}{Q_i}\right) \quad (1)$$

KLD was systemized by calculating KLD(P|Q) and KLD (Q|P), and averaging them $$KLD(P, Q) = \frac{KLD(P|Q) + KLD(Q|P)}{2} \quad (2)$$

The statistical significance of the KLD value was determined using a null distribution generated by 105 KLD values estimated from random pairs of genes (regardless of whether they share a network edge), providing a p-value for the dysregulation of the edges in the network Using the dysregulation score for the interactions in a network the regulatory changes imposed by the genes were evaluated. This can be done by combining the p-values obtained from the KL-divergence of the interactions surrounding that gene using Fisher's method which transforms a set of k p-values, $pv_i$ (i=1 . . . k), obtained from the k interactions surrounding a given gene into a chi-square statistic $$X^2 = -2\Sigma_{i=1}^{k} \log(pv_i) \quad (3)$$

The combined p-value is then calculated using chi-square distribution with 2k degrees of freedom. One of the underlying assumption in combining p-values using Fisher's method is independence, i.e., it assumes that the interactions surrounding a gene are independent and therefore the p-values for these interactions being dysregulated following compound perturbation is also independent. Since the interactions surrounding a given gene, a, has that gene in common, a dependency between these interactions cannot be ruled out. Therefore, Brown's method was applied for correction of p-value dependence, which utilizes the covariance matrix from the original data to correct both the variance and the degrees of freedom needed to obtain the p-value from the chi-square statistic. Since one has to correct the dependency between interactions and not between the genes the covariance between the residuals from a linear fit to the common gene, a was used (see FIG. 12A). This correction removes bias in the estimation of p-values for dysregulation of genes associated with high number of interactions in the network (see FIG. 12B). Specifically, the variance of the chi-square can be redefined as $$\sigma^2(\chi^2) = 4k + \Sigma_{i=1}^{k}\Sigma_{j=i+1}^{k}\varphi(\rho_{ij}) \quad (4)$$

where $\rho_{ij}$ is the correlation between the residuals of gene i and gene j, and $$\varphi(p_{ij}) = \begin{cases} \rho_{ij}(3.25 + 0.75\rho_{ij}) & 0 \leq \rho_{ij} \leq 1 \\ \rho_{ij}(3.27 + 0.71\rho_{ij}) & -0.5 \leq \rho_{ij} \leq 0 \end{cases} \quad (5)$$

Using this variance, the degrees of freedom can be redefined to be $$df = \frac{8k^2}{\sigma^2(X^2)} \quad (6)$$

And one can use this to get a corrected p-value which was corrected for multiple hypothesis testing using Benjamini-Hochberg procedure.

The knowledge of direct targets for the compounds was obtained from the DrugBank database, the MATADOR database, and literature. From the MATADOR database, genes annotated as 'direct' or 'direct-indirect' were considered as known targets for a compound, while genes labeled as 'indirect' were discarded. For a list of targets of the compounds used in this study.

A sub-sampling analysis was performed to evaluate DeMAND's performance with varying number of GEP. This is done by first randomly sampling i, (i=3.18) samples from the 18 compound treated samples and same number of i samples from the 24 control samples for each compound in DP14 dataset and running DeMAND on these i samples. For each compound and for each i, this is repeated 10 times and the 10 results obtained from sub-sampled data are compared with the result obtained using the samples using a McNemar test. McNemar test checks for homogeneity between two results, while considering the fact that the two results under consideration were obtained from overlapping samples.

To test if compound pairs predicted to be similar by DeMAND also share a similar therapeutic class, pharmacological/therapeutic information for each compound from the Anatomical Therapeutic Chemical (ATC) classification system was used. Specifically, the $2^{nd}$ level ATC classification, depicting pharmacological/therapeutic subgroup information to each compound was used. If a given compound pair shared the same code then they were considered to share similar therapeutic class.

Of the 92 compounds in DP92 dataset, 10 of them were also profiled in $CTD^2$. Among all potential pairs of compound combinations between these 10 compounds, 5 compound pairs didn't have sensitivity profiles for the same cell line, so similarity among them could not be accessed. For the remaining 40 compound pairs, similarity was accessed from sensitivity profile using at least 23 common cell lines to a maximum of 237 cell lines. The similarities between the compounds were measured by Pearson's correlation of the sensitivity profiles and its significance was estimated by t-distribution with the degrees of freedom equals to the number of common cell lines −2.

To evaluate the similarity between the DeMAND predictions of two compounds, the significantly DPGs (FDR≤0.1) in the DeMAND results for each compound were selected. Then Fisher exact test was applied using these selected genes to compute the significance of overlap between them. A large number of common genes were found with no significant p-value across the compounds, which resulted in high overlap of negative gene set between compound pairs in Fisher exact test, thus causing a bias in the similarity estimation. To correct this bias the genes that never showed a significant score to be part of MoA across the entire panel of compounds were removed from the background set, and Fisher-exact test was recomputed. This correcting had no effect on the ranking of compound pairs from most similar to least but only on the similarity estimation by providing corrected p-values.

To obtain p-value for similarity for each compound pair in DP92 dataset the p-values for similarity for 3 cell lines were calculated independently and Fisher's method was used to combine these p-values.

To evaluate if change in the sensitivity of the underlying network had an effect on DeMAND's performance a gradient analysis was performed. To do this, the interactions were gradually removed randomly from the network and DeMAND's output was compared with the output obtained using the network using Fisher exact test. This test was performed independently on 14 compounds from the DP14 dataset. Due to computational constrained the interactions were removed in a step wise fashion starting by removing 10% of the interactions, followed by removing an additional 10% of the interaction, and continuing until only 10% of the interactions are left in the network.

For each compound and each method (either DeMAND or t-test) the true-positive and the false-positive rates were calculated as a function of the fraction of top genes. For a compound with d direct targets, considering the top n genes with the most significant p-value by a method, true-positive rate (TPR, also known as sensitivity) is defined as the fraction of known direct targets for that compound predicted by the method and false-positive rate (FPR) is defined as the fraction of genes that are not known direct targets among the same n genes.

$$TPR = \frac{p}{d}; FPR = \frac{n-p}{N-d} \quad (7)$$

where p is the number of direct targets of the compounds predicted in the top n predictions by the method and N is the total of number of genes profiled in a given GEP dataset. Since DeMAND provides a p-value for genes that are in the network, the calculation of both the rates was terminated when the network size was reached, and the curves were assumed to continue using random rank assignment to end point in which both rates are equal to one. This is depicted in the ROC curves as a straight line connecting the point at which the network size was reached with the theoretical maximum TPR and FPR value of 1.

Note that in the GEODB different expression sets are obtained from different platforms, and therefore both the total number of genes that can be predicted and the number of genes in the network varies. To obtain the average sensitivity curves (in both datasets) we therefore averaged both the true-positive and false-positive rates according to the fraction of top genes out of the total available genes in that platform (instead of using the number of top genes).

The diffuse large B-cell lymphoma (DLBCL) cell lines OCI-LY3 and OCI-LY7 were obtained from University Health Network (Toronto, Canada); the U-2932 DLBCL cell line was purchased from the Leibniz-Institute DSMZ German Collection of Microorganisms and Cell Cultures; the U-2-OS osteosarcoma cell line was obtained from ATCC (Cat #ATCC HTB-96). OCI-LY3, OCI-LY7, U-2932 cell lines were cultured in Iscove's Modified Dulbecco Medium (IMDM) supplemented with 10% fetal bovine serum at 37° C. in a 5% $CO_2$ atmosphere whereas the U-2-OS cells were cultured in McCoy's 5A medium supplemented with 10% fetal bovine serum.

Compounds were selected based on their activity in a primary screen of FDA-approved, late-stage experimental, and tool compounds. OCI-LY3, OCI-LY7 and U-2932 cells were seeded in white, tissue culture-treated 96-well plates at a density of $5 \times 10^4$ cells per well in 100 µL total volume using the Janus automated liquid handling system (Perkin Elmer Inc.). After 12 hrs of incubation at 37° C. the plates were allowed to cool to room temperature prior to compound addition via the Janus. Compounds were transferred as 1 µL of DMSO stock solutions into the assay plates (plate based triplication), which were subsequently placed on an orbital shaker for 5 minutes and then placed back in the incubator. After 24 hrs the plates were removed from the incubator and equilibrated to room temperature before addition of 50 µL of CellTiter-Glo Luminescent Cell Viability Assay (Promega Corp.) per well. Plates were shaken 5 minutes on an orbital shaker before data acquisition in an Envision (PerkinElmer Inc.) (0.5 second read time, enhanced luminescence). $IC_{20}$ values were determined using IDBS Activity Base utilizing a four parameter fit model.

For each compound, a stock concentration of the $IC_{20}$ at 24 hrs was created by dilution in DMSO. Cells were seeded in tissue culture-treated 96-well plates at a density of $5 \times 10^4$ cells per well using the Janus automated liquid handling system (Perkin Elmer, Inc.) and treated with the 24 hrs $IC_{20}$ of each of the compounds for 6, 12, and 24 hrs at 37° C., 5% $CO_2$ under humidified conditions. For each compound/ condition combination one single data point was analyzed and 0.2% DMSO vehicle treated samples were used as controls. Viability assay was run in parallel to monitor the compound effectiveness.

Total RNA was isolated with the RNAqueous-96 Automated Kit (Ambion) on the Janus automated liquid handling system (Perkin Elmer Inc.), quantified by NanoDrop 6000 spectrophotometer and quality checked by Agilent Bioanalyzer. 300 ng of each of the samples with RIN value >7 were converted to biotinylated cRNA with the Illumina TotalPrep-96 RNA Amplification Kit (Ambion) using a standard T7-based amplification protocol and hybridized on the Human Genome U219 96-Array Plate (Affymetrix). Hybridization, washing, staining and scanning of the array plates were performed on the GeneTitan Instrument (Affymetrix) according to manufacturer's protocols.

Small interfering RNA (siRNA) targeting each specified gene and siControl SMARTpools were obtained from Dharmacon Technologies (see Table 3). Reverse transfection was performed by preparing a solution of 1 mL of Opti-MEM (Invitrogen), 64, of Lipofectamine-RNAiMAX reagent (Invitrogen) and 1.25 μL of 10 μM RNAi solution (final working concentration is 6.4 nM), and incubating the mixture (1 mL/well) in a 6-well dish for 20 minutes at 37° C. U-2-OS cells were detached from culture flask, and resuspended in 2× serum-containing media at a density of $4 \times 10^5$ cells/mL. One mL of cell suspension was transferred to each well containing the transfection mixture, and the 6-well plate was returned to culture incubator. After 48 hrs, cells were detached and reverse transfected again using the same procedures. After 48 hrs, cells were trypsinized and reseeded into 384-well format to determine sensitivity against vincristine. After 48 hrs of vincristine treatment, 10 μL of 50% alamar Blue (Life Technologies) solution in U-2-OS growth media was transferred to the 384-well plates, which resulted in 10% final concentration alamar Blue. Plates were incubated further for 16 hrs to allow reduction of alamar Blue, which results in the generation of red fluorescence. The fluorescence intensity was determined using a Victor 3 plate reader (Perkin Elmer, Inc.), and used to calculated percent growth inhibition.

TABLE 3

Table 3: siRNA for Vincristine MoA GRUAF Custom Plate Order Number 2344676.1

| Plate | Well | Pool Catalog Number | Duplex Catalog Number | Gene Symbol | GENE ID | Gene Accession | GI Number | Sequence |
|---|---|---|---|---|---|---|---|---|
| Plate 1 | A02 | L-003206-00 | J-003206-09 | CCNB1 | 891 | NM_031966 | 34304372 | CAACAUUAC CUGUCAUAU A (SEQ ID NO: 1) |
| Plate 1 | A02 | L-003206-00 | J-003206-10 | CCNB1 | 891 | NM_031966 | 34304372 | UGCACUAGU UCAAGAUUU A (SEQ ID NO: 2) |
| Plate 1 | A02 | L-003206-00 | J-003206-11 | CCNB1 | 891 | NM_031966 | 34304372 | GAAUGUAGU CAUGGUAAA U (SEQ ID NO: 3) |
| Plate 1 | A02 | L-003206-00 | J-003206-12 | CCNB1 | 891 | NM_031966 | 34304372 | CUAAUUGAC UGGCUAGUA C (SEQ ID NO: 4) |
| Plate 1 | A03 | L-013603-01 | J-013603-13 | RPS3A | 6189 | NM_001006 | 70609888 | GGCAAGAAC AAGCGCCUU A (SEQ ID NO: 5) |
| Plate 1 | A03 | L-013603-01 | J-013603-14 | RPS3A | 6189 | NM_001006 | 70609888 | GCAACAAUC AGAUACGGA A (SEQ ID NO: 6) |
| Plate 1 | A03 | L-013603-01 | J-013603-15 | RPS3A | 6189 | NM_001006 | 70609888 | GAUUGAAGC UCACGUUGA U (SEQ ID NO: 7) |
| Plate 1 | A03 | L-013603-01 | J-013603-16 | RPS3A | 6189 | NM_001006 | 70609888 | UCAAGACUA CCGAUGGU UA (SEQ ID NO: 8) |

TABLE 3-continued

Table 3: siRNA for Vincristine MoA
GRUAF Custom Plate
Order Number 2344676.1

| Plate | Well | Pool Catalog Number | Duplex Catalog Number | Gene Symbol | GENE ID | Gene Accession | GI Number | Sequence |
|---|---|---|---|---|---|---|---|---|
| Plate 1 | A04 | L-003936-00 | J-003936-09 | VHL | 7428 | NM_198156 | 38045905 | AGGCAGGCGUCGAAGAGUA (SEQ ID NO: 9) |
| Plate 1 | A04 | L-003936-00 | J-003936-10 | VHL | 7428 | NM_198156 | 38045905 | CCACCCAAAUGUGCAGAAA (SEQ ID NO: 10) |
| Plate 1 | A04 | L-003936-00 | J-003936-11 | VHL | 7428 | NM_198156 | 38045905 | GGAGCGCAUUGCACAUCAA (SEQ ID NO: 11) |
| Plate 1 | A04 | L-003936-00 | J-003936-12 | VHL | 7428 | NM_198156 | 38045905 | CCAAUGGAUUCAUGGAGUA (SEQ ID NO: 12) |
| Plate 1 | A05 | L-004765-00 | J-004765-05 | NFKBIA | 4792 | NM_020529 | 10092618 | AGUCAGAGUUCACGGAGUU (SEQ ID NO: 13) |
| Plate 1 | A05 | L-004765-00 | J-004765-06 | NFKBIA | 4792 | NM_020529 | 10092618 | GCUGAUGUCAACAGAGUUA (SEQ ID NO: 14) |
| Plate 1 | A05 | L-004765-00 | J-004765-07 | NFKBIA | 4792 | NM_020529 | 10092618 | AGGACGAGCUGCCCUAUGA (SEQ ID NO: 15) |
| Plate 1 | A05 | L-004765-00 | J-004765-08 | NFKBIA | 4792 | NM_020529 | 10092618 | GUGCUGAUGUCAAUGCUCA (SEQ ID NO: 16) |
| Plate 1 | A06 | L-010325-00 | J-010325-06 | TUBB | 203068 | NM_178014 | 34222261 | GGAAUGGGCACUCUCCUUA (SEQ ID NO: 17) |
| Plate 1 | A06 | L-010325-00 | J-010325-07 | TUBB | 203068 | NM_178014 | 34222261 | AAGAAUACCCUGAUCGCAU (SEQ ID NO: 18) |
| Plate 1 | A06 | L-010325-00 | J-010325-08 | TUBB | 203068 | NM_178014 | 34222261 | UCCAUCAGUUGGUAGAGAA (SEQ ID NO: 19) |
| Plate 1 | A06 | L-010325-00 | J-010325-09 | TUBB | 203068 | NM_178014 | 34222261 | CCGCAUCUCUGUGUACUAC (SEQ ID NO: 20) |

Cells were grown on coverslips to ~50% confluency and treated with compounds for 24 hrs. Cells were fixed with 3.7% formaldehyde solution in PBS for 15-30 minutes followed by washing with PBS 5 times. Cell membrane was permeabilized with 0.2% Triton-X in PBS for 10 minutes and rinsed once with TBS (10 mM Tris [pH 7.5], 150 mM NaCl). The permeabilized sample was blocked with 10% goat serum in TTBS (0.1% Tween-20 in TBS) for 30-60 minutes and washed once with TTBS. The microtubule network was probed with anti-tubulin antibody (Santa Cruz cat #sc-32293) in 1% goat serum in TTBS for 30-60 minutes at room temperature followed by washing in TTBS for 10 minutes. Alexa Fluor anti-mouse antibody (Invitrogen, cat #A-11005) was used as the secondary antibody to visualize the microtubule network using the 60× lens of a confocal microscope.

GPX4 enzymatic activity assay was performed as follows. Briefly, $1 \times 10^6$ cells were re-suspended in the cell lysis buffer. Sonication was used to make cell lysates followed by centrifugation at 14,000 rpm for 10 minutes. Protein concentration of the cleared cell lysates was determined using a Bradford protein assay (Bio-Rad). Two hundred micrograms of cellular proteins was mixed with phosphatidyl choline hydroperoxide (PC—OOH), the GPX4 specific substrate, and reduced glutathione, a GPX4 cofactor. The mixture was incubated at 37° C. for 30 minutes followed by lipid extraction using a chloroform:methanol (2:1) solution. The lipid extract was evaporated using a rotary evaporator, and re-dissolved in 100% ethanol before injecting into LC-MS instrument for PC-OOH quantitation.

U-2932 cells were seeded in 10 cm dish ($2 \times 10^6$/dish) and grown at 37° C. for 16 hrs. Cells were treated with vehicle (0.4% DMSO), 1 mM sulfasalazine (24 hr $IC_{50}$) or 1 mM altretamine (double the 24 hr $IC_{50}$), and incubated for 24 hrs. Cells were then harvested, pelleted, washed once with 400 µl ice-cold PBS containing 1 mM EDTA and sonicated. After the debris was pelleted and removed, both oxidized and reduced glutathione in 120 µL of sample was quantified in technical triplicate using QuantiChrome glutathione assay kit (BioAssay Sytems). The glutathione quantity was normalized to protein concentration measured with Bradford assay (Bio-Rad).

U-2932 cells ($2 \times 10^5$) were seeded in 6-well plates and incubated at 37° C. for 16 hrs. Cells were treated with test compounds for the indicated time, then harvested, pelleted and washed once with PBS. For lipid ROS detections, cells were re-suspended with Hanks Balanced Salt Solution (HBSS, Life Technologies) containing C11-BODIPY (581/591) (2 µM) (Life Technologies) and incubated for 10 minutes at 37° C. Cells were then pelleted, re-suspended in 500 µL HBSS, strained through 40 µM cell strainer (BD Falcon), and analyzed using BD Accuri C6 flow cytometer (BD Biosciences). C11-BODIPY signal was measured using FL1 channel. Experiments were done in biological triplicates, and a representative result was shown.

The JAK2-selective inhibitor TG101348 and Mitomycin C was purchased from Selleckchem and Tocris Bioscience respectively and were and dissolved in DMSO. OCI-LY3 cells were treated with the indicated compounds in 96-well plates and there growth was determined using the CellTiter-Glo Luminescent Cell Viability Assay (Promega Corp). Typically, 30,000 OCI-Ly3 cells per well in 200 µL of growth medium were grown for 48 hrs in the presence or absence (DMSO alone) of the desired compounds, and then assayed with CellTiter Glo according to manufacturer's instructions.

Figure 3:
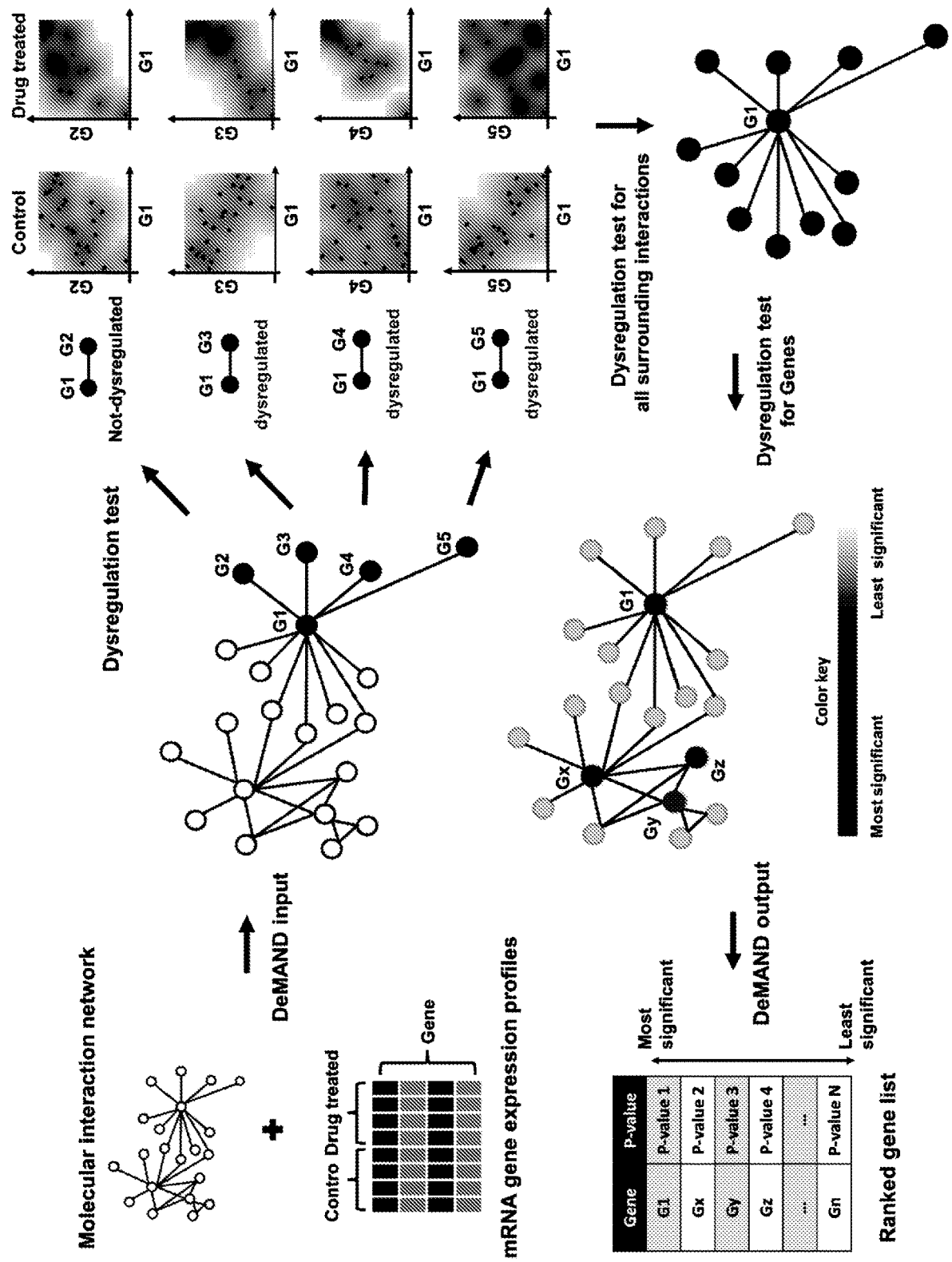
FIG. 3 illustrates schematics of an exemplary algorithm in accordance with the disclosed subject matter.

Referring to FIG. 3 for the purpose of illustration and not limitation, DeMAND can accept as input a regulatory network in combination with gene expression profiles from control samples and perturbed samples. Using this input each interaction in the network is individually tested for dysregulation. This is done by first smoothing the co-expression scatter plot for the two genes involved in the interaction using a Gaussian kernel method (i.e. replacing each expression value in the two-dimensional plot with a two dimensional Gaussian around that value), thus obtaining an estimation of the underlying probability density. The difference between the probability distributions of control and perturbed samples is evaluated using KL divergence, and the statistical significance of this difference is determined by comparing this value with KL divergence values of random gene pairs. Next, the dysregulation of each gene in the network is determined by integrating the p-values of its interactions, while taking into account the dependency between them (see also FIG. 12), thus providing a single score reflecting the significance of dysregulation of the gene. As output, DeMAND provides a list of the genes in the input data and the p-value associated with their dysregulation.

Figure 4A:
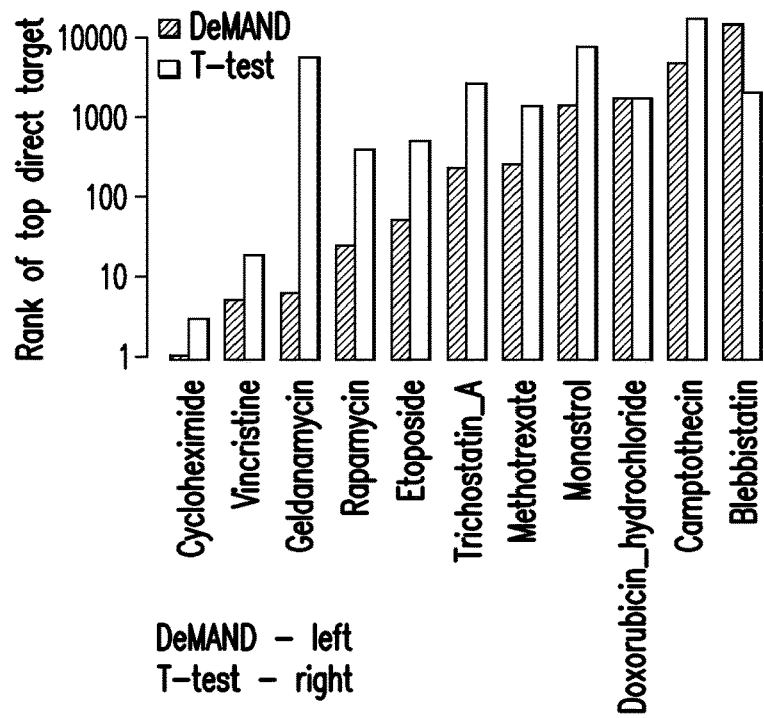
FIG. 4 illustrates a comparison between a disclosed embodiment and t-test and biological representation predictions.
Figure 4B:
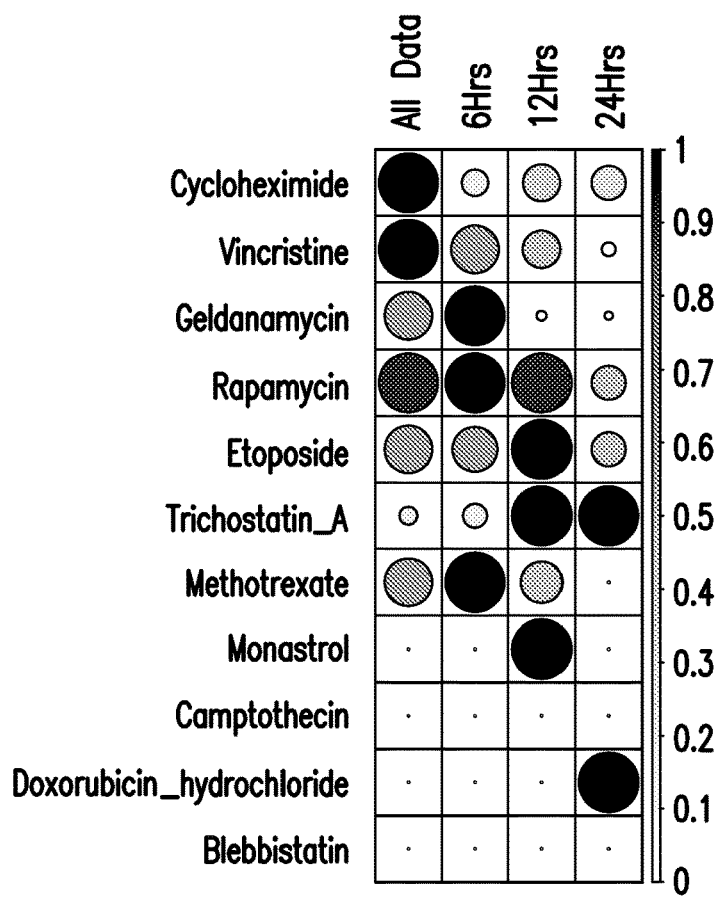
Figure 4C:
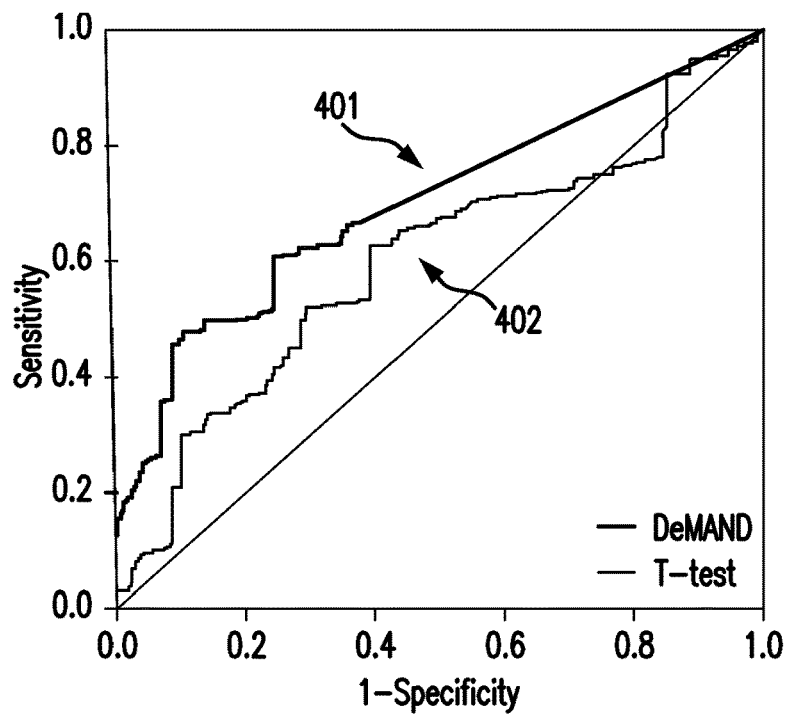
Figure 5:
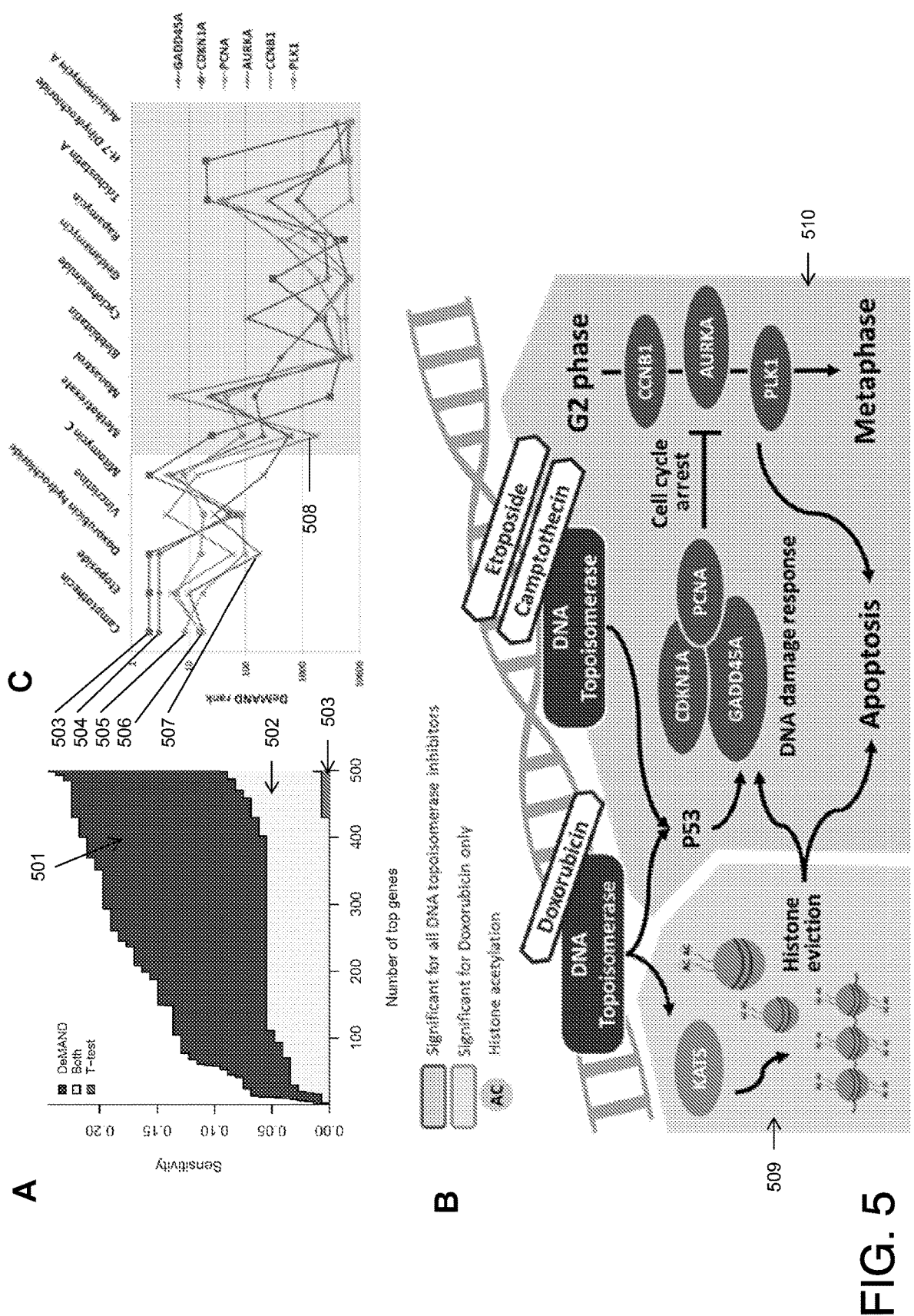
FIG. 5 illustrates example results for the DP14 dataset.

FIG. 4A shows, for the purpose of illustration and not limitation, the best rank of known direct targets for each compound in the DP14 dataset as predicted by DeMAND (left) and by t-test (right). DeMAND identifies known targets at a better rank for 10 out of the 11 compounds.

Referring to FIG. 4B for the purpose of illustration and not limitation, the normalized best rank of known direct targets for each compound in the DP14 dataset as predicted by DeMAND using GEPs from each time point together (e.g., all Data) or using GEP for each time point independently (6 hrs, 12 hrs or 24 hrs). Normalization is done for each individual compound by taking the ratio of minimum rank across the four predictions (all Data, 6 hrs, 12 hrs or 24 hrs) and the rank of each of four predictions. Size/color of each circle represents the normalized rank, where a bigger or darker circle represents the lower rank or better prediction. The figure shows the normalized rank only for predictions with FDR≤0.1.

FIG. 4C shows, for the purpose of illustration and not limitation, the average true-positive rate (sensitivity) as a function of the false-positive rate for identifying known direct targets for the compounds in the DP14 dataset using the DeMAND predictions (401) and using a t-test analysis (402). For each value of false-positive rate shown, DeMAND achieves a higher true-positive rate than a t-test. The straight line at the top-right for the DeMAND predictions indicates a random rank assignment for genes that are not in the regulatory network.

Figure 4D:
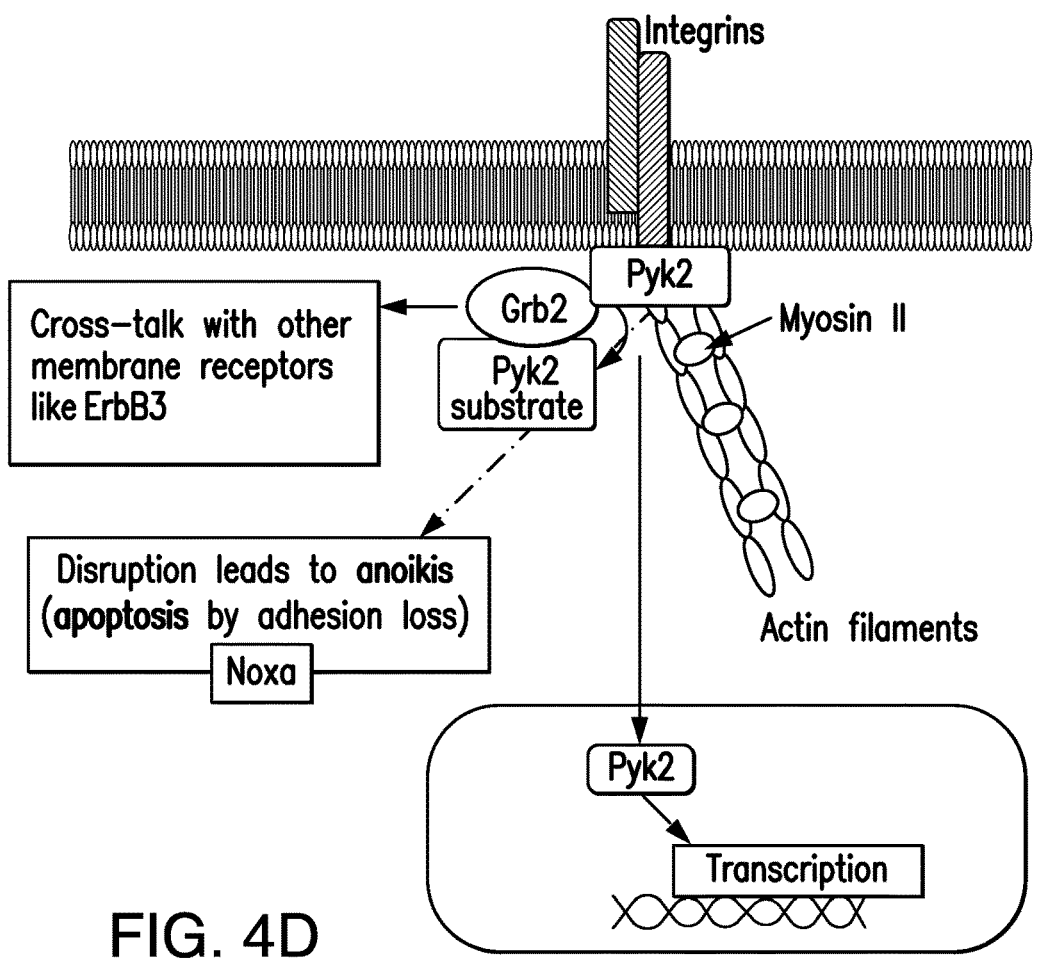

Referring to FIG. 4D for the purpose of illustration and not limitation, blebbistatin is a specific inhibitor of Myosin II, which is a non-muscle myosin, involved in integrin signaling. In B cells, myosin II is critical to B cell receptor signaling and immunological synapse stability, cell-to-cell contact, chemotaxis, cell cycle and cell division. Pyk2/PTK2B is a key kinase regulating myosin II phosphorylation and is activated by integrin or chemokine-mediated Ca+2 signaling, as well as reactive oxygen species (ROS) generation in stress, leading to Src-family kinase association (FYN) through the GRB2 adapter gene. Although DEMAND does not predict myosin II as an MoA of blebbistatin, it predicts PTK2B, FYN, and GRB2 as MoA genes.

Figure 4E:
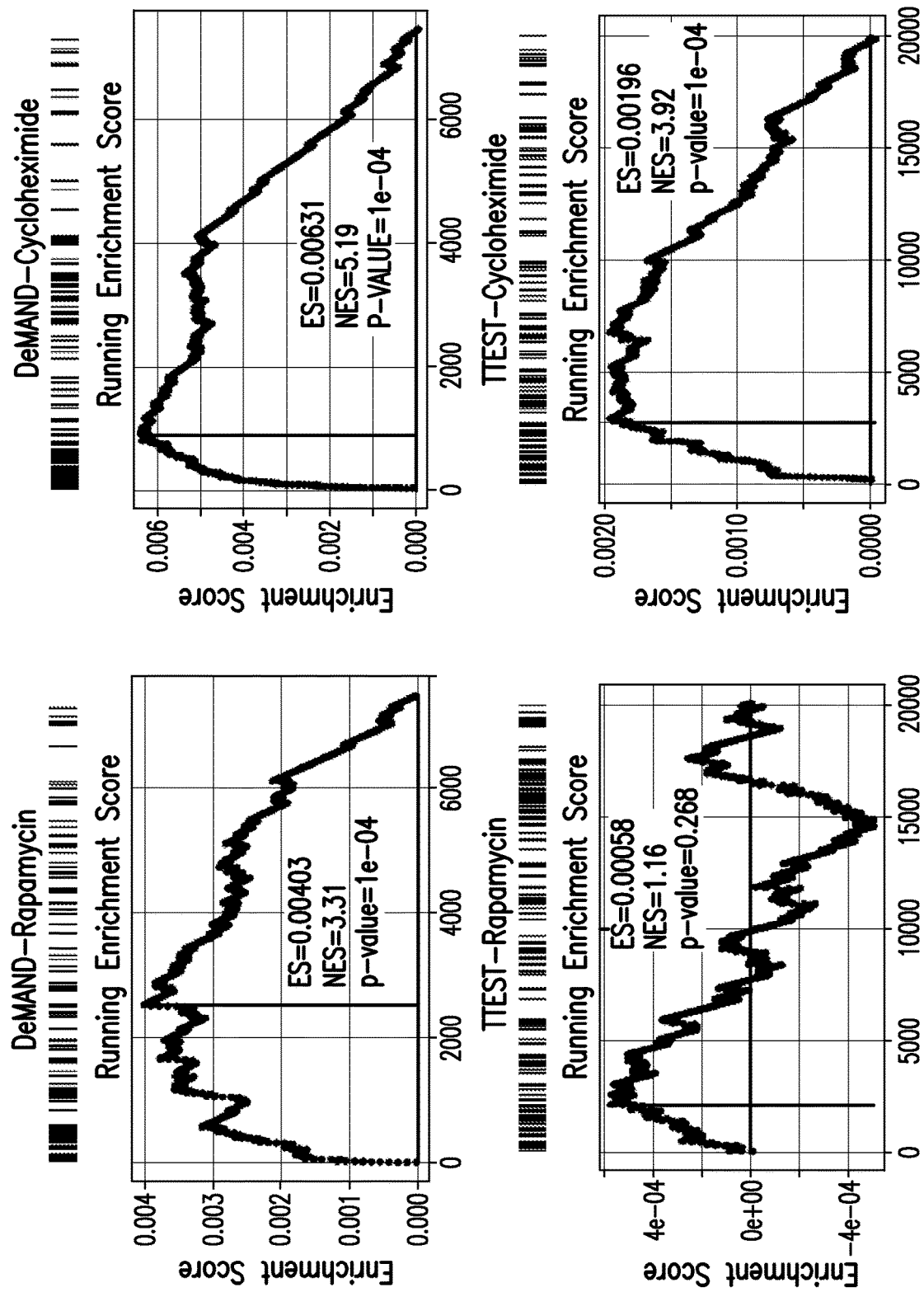

FIG. 4E shows, for the purpose of illustration and not limitation, GSEA plots showing the enrichment of a rapamycin response gene set for compounds that are known to affect MTOR, namely rapamycin (top-left and bottom-left) and cycloheximide (top-right and bottom-right). When the genes are ranked according to DeMAND predictions (top) the enrichment is statistically significant for the two compounds. When sorting using the t-test prediction no significance is observed for rapamycin (bottom-left), while statistical significance remains for cycloheximide (bottom-right).

FIG. 5A illustrates, for the purpose of illustration and not limitation, the average sensitivity (true-positive rate) of identifying known direct targets for all the compounds in the DP14 dataset using DeMAND (501 and 502) and using a t-test analysis (503 and 502), as a function of the number of top predictions. DeMAND outperforms the t-test analysis for a number of top genes. For example, DeMAND achieves almost 15% sensitivity in the top 100 predictions, while t-test achieves only 3% sensitivity. Furthermore, most direct targets that are identified by a t-test analysis are also identified by DeMAND, as demonstrated by the lack of red until over 400 of the top genes are selected. The opposite is not true, and DeMAND identifies many direct targets that are not identified by t-test, as exemplified by the large blue area.

FIG. 5B shows, for the purpose of illustration and not limitation, a schematic comparing the MoA of three topoisomerase inhibitors—camptothecin, doxorubicin, and etoposide, focused on genes predicted to participate in the MoA of each compound by DeMAND. Genes that are unique for doxorubicin are in the area with the orange background (509), while genes that are unique for camptothecin and etoposide are in the area with the purple background (510). The compounds share the main DNA-damage repair MoA including GADD45A, PCNA, and CDNK1A. The doxorubicin MoA includes KAT5, which is involved in histone eviction, and SIK1, which is involved in maintenance of cardiac progenitor cells, and thus links doxorubicin to its most prominent therapy-limiting side effects of cardiomyopathy.

FIG. 5C shows, for the purpose of illustration and not limitation, DeMAND predicted rank for genes involved in the DNA damage response. DeMAND predicts GADD45A (504), the canonical DNA-damage-inducible gene and its well-known interactor genes, CDKN1A (503), PCNA (505), CCNB1 (508), AURKA (507), and PLK1 (506) among the statistically significant MoA-inferred genes for 5 of the DNA damaging agents (i.e., camptothecin, doxorubicin, etoposide, mitomycin C, and vincristine) specifically.

FIG. 6A shows, for the purpose of illustration and not limitation, a visualization of microtubule network by immunohistochemistry for cells treated with DMSO, vincristine, non-specific siRNA, and siRNA targeting RPS3A. Non-specific siRNA has no effect on the microtubule network compared to the DMSO control. Both vincristine and siRPS3A significantly altered microtubule network. U-2-OS cells were treated with 4 nM of vincristine for 24 hrs.

FIG. 6B shows, for the purpose of illustration and not limitation, the percent of cell inhibition as a function of vincristine concentration compared to siRNA transfected cells without vincristine treatment for U-2-OS cells treated with non-specific siRNA (602), siRNA targeting CCNB1 (604), VHL (601), NFKBIA (603), and RPS3A (605). Inhibition of RPS3A and of CCNB1 reduces the cell sensitivity to vincristine treatment, while inhibition of VHL increases the sensitivity two-folds.

FIG. 6C shows, for the purpose of illustration and not limitation, the percent of cell inhibition compared to DMSO treatment as a function of mitomycin C concentration for OCI-LY3 cells treated with mitomycin C alone (empty circle) or with mitomycin C in combination with JAK2 inhibitor using 0.2 uM (filled in circle), 0.4 uM (inverted triangle), and 0.6 uM (square). JAK2 inhibitor levels are correlated with reduction in the sensitivity of the cells to mitomycin C treatment.

Figure 7A:
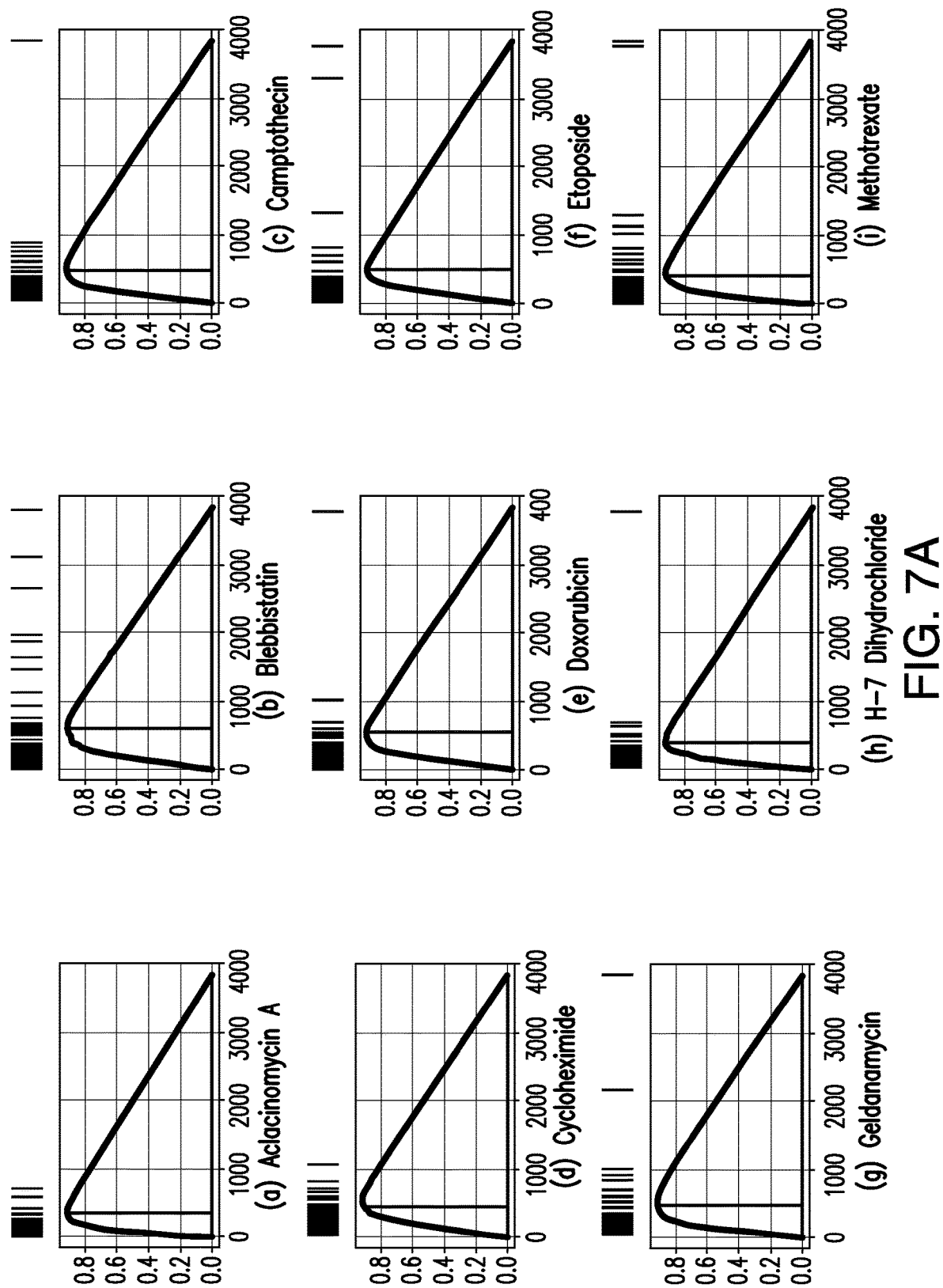
FIG. 7 illustrates identifying minimum requirements to run a disclosed embodiment.
Figure 7A:
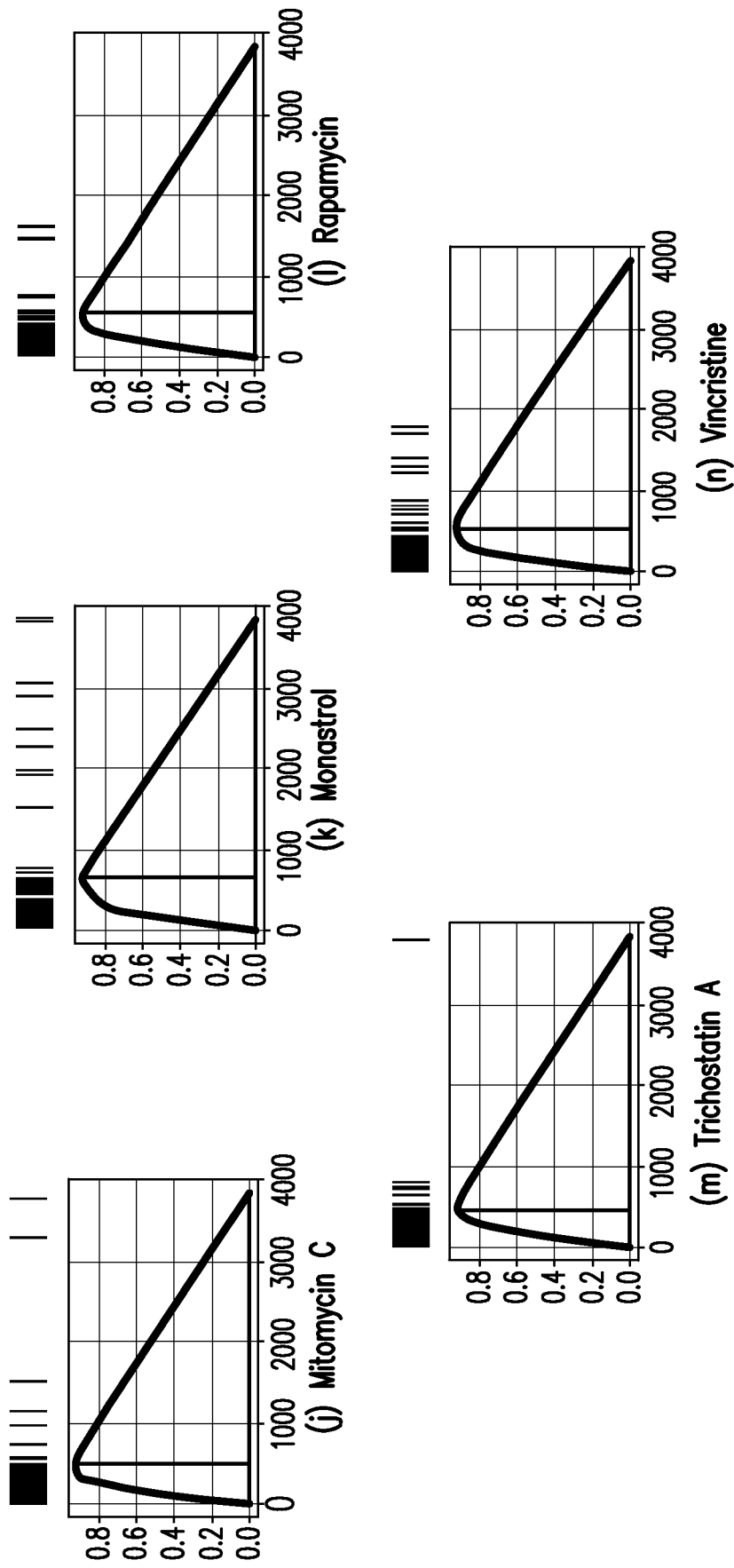

FIG. 7A shows, for the purpose of illustration and not limitation, GSEA plots of the significant DeMAND results for each compound in the DP14 dataset when using the U95av2 regulatory network, where the ranking is according to the results using the U133p2 regulatory network. The compounds show a statistical significance (p-values$\leq 10^{-9}$) exemplifying that the DeMAND results are not sensitive to the input network.

Figure 7B:
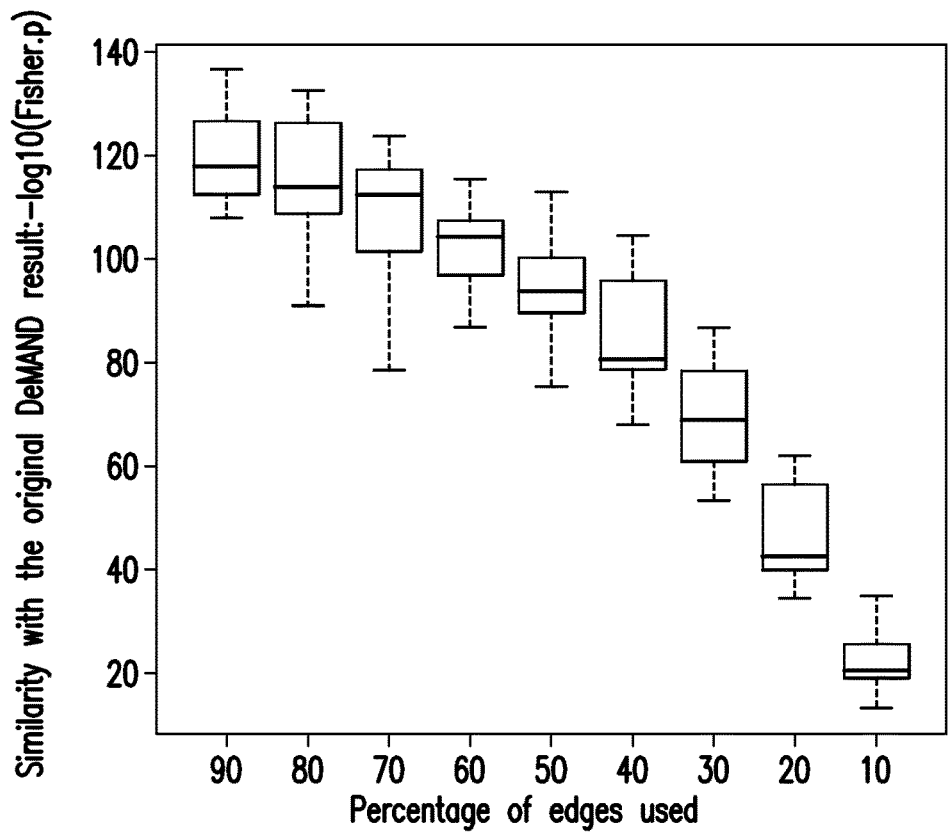
Figure 7C:
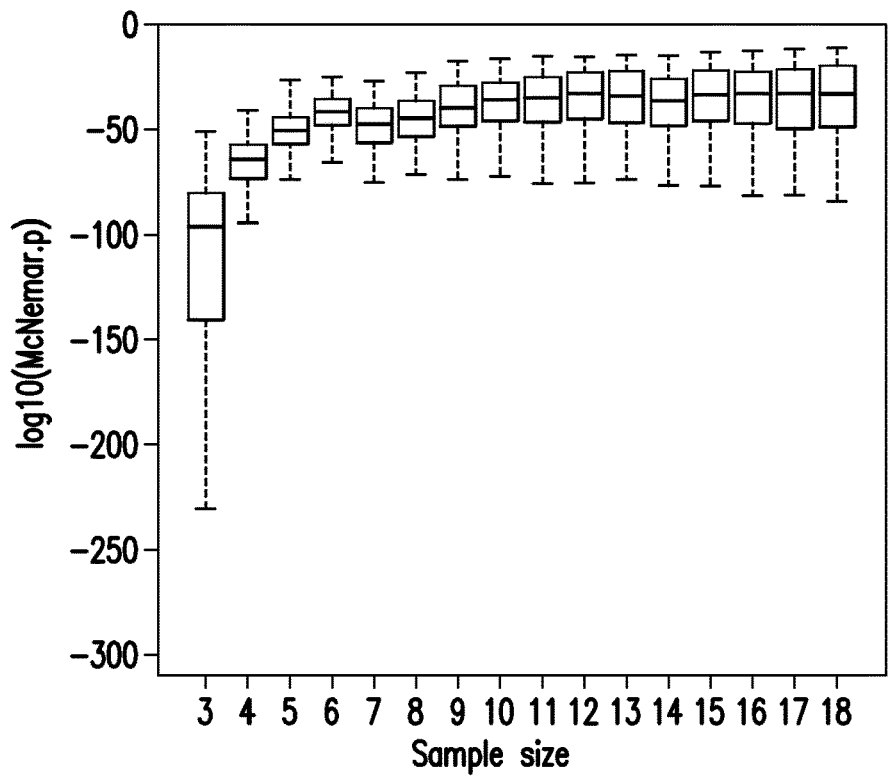

Referring to FIG. 7B for the purpose of illustration and not limitation, DeMAND was applied to the DP14 dataset after randomly removing interactions from the network, and the significant results were compared with the original results using Fisher exact test. The plot shows the log 10 of the p-value of the Fisher exact test as a function of percentage of the edges that were removed. The p-values of the overlap drop below statistical significance (after multiple hypothesis correction) only after over 60% of the interactions are removed.

Referring to FIG. 7C for the purpose of illustration and not limitation, DeMAND was applied to the DP14 dataset using bootstrapped subsets of the control and perturbed data, and the significance of the difference from the results using 18 samples and 18 control samples was evaluated using a McNemar test (in which a large difference provides a significant p-value). The plot shows the log 10 of the p-value as a function of the sample size. For sample sizes of 6 and above the p-values are within a single standard deviation from the results using 18 samples.

Figure 8A:
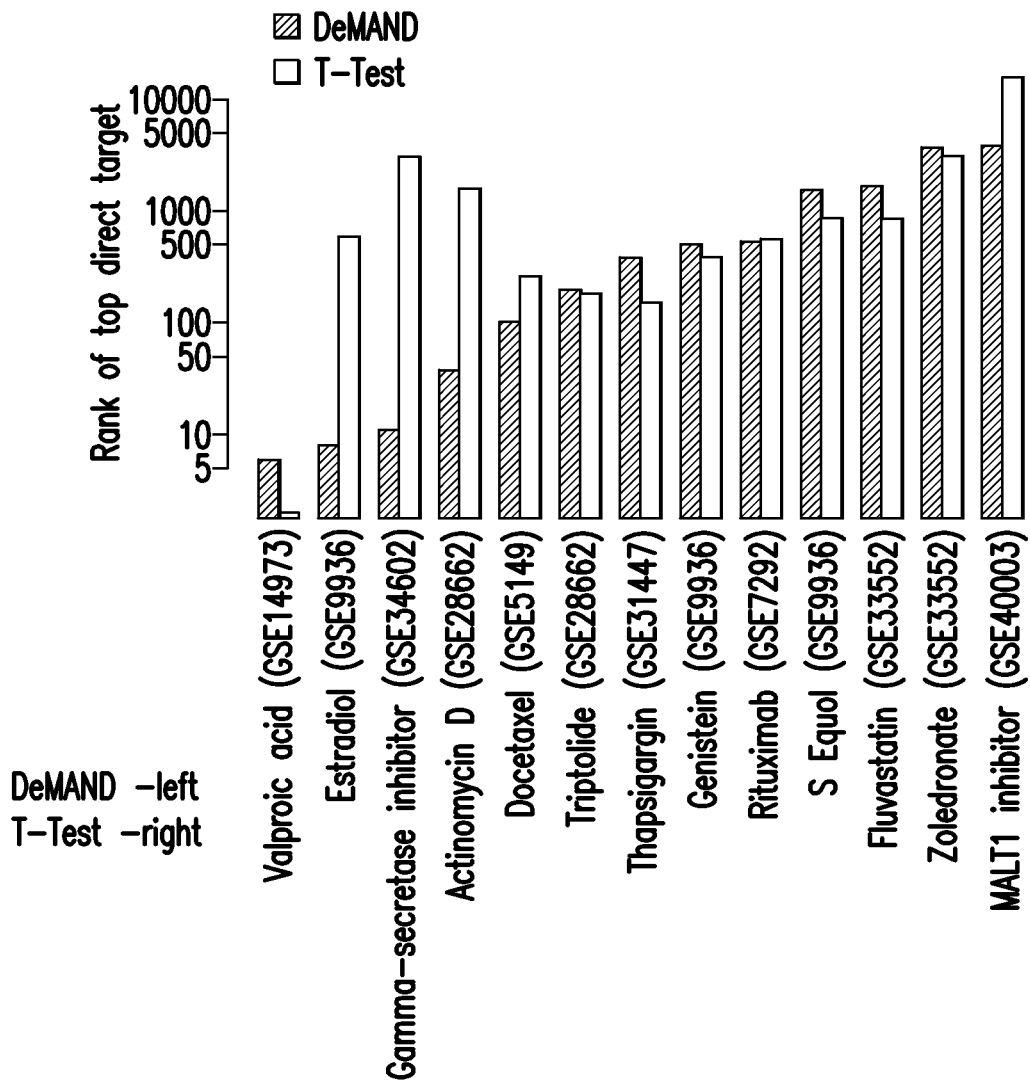
FIG. 8 illustrates example results from GEO datasets.
Figure 8B:
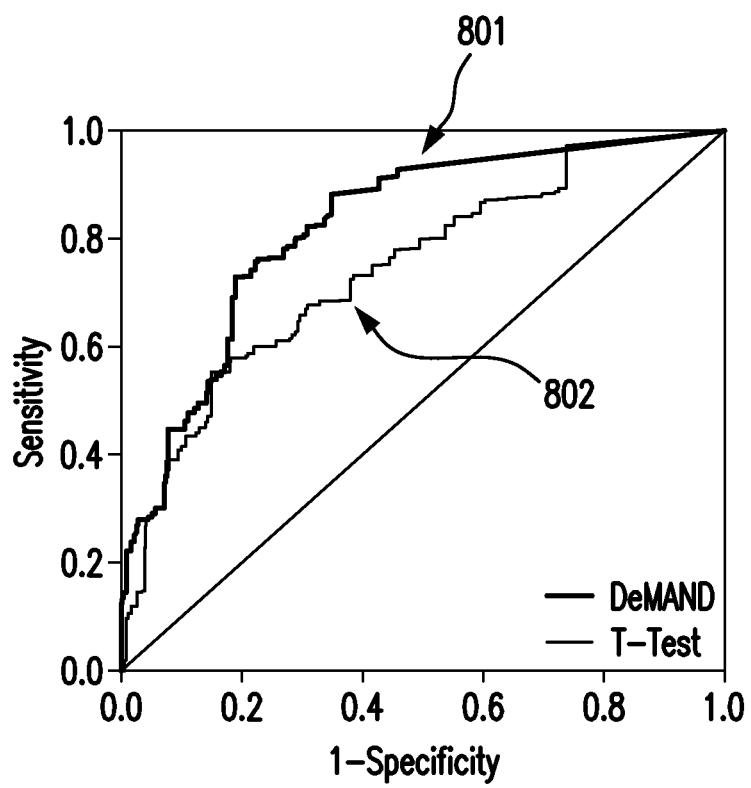
Figure 8C:
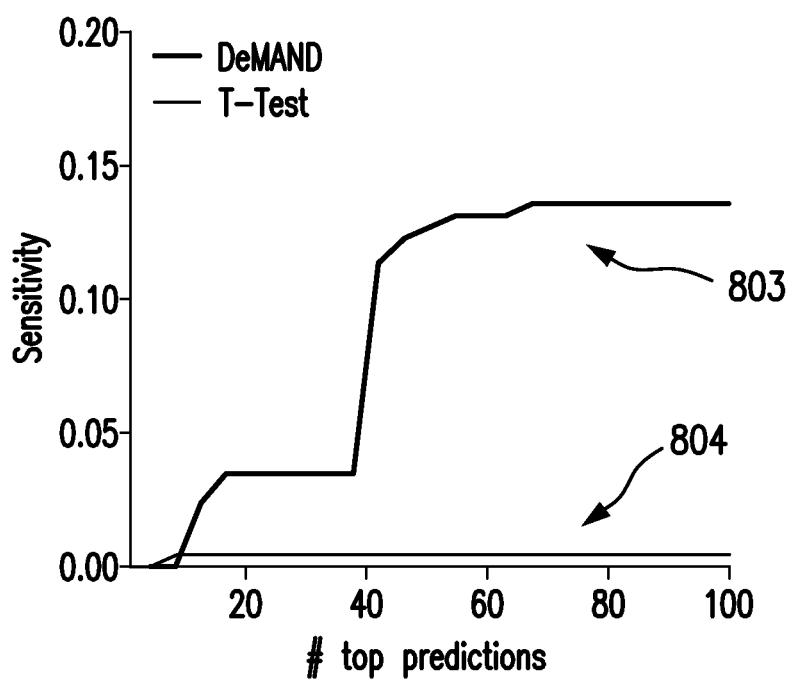

FIG. 8A shows, for the purpose of illustration and not limitation, the best rank of a known direct target for each compound in the GEODB dataset as predicted by DeMAND (left) and by t-test (right).

FIG. 8B shows, for the purpose of illustration and not limitation, the average true-positive rate (sensitivity) as a function of the false-positive rate for identifying known direct targets for the compounds in the GEODB dataset using the DeMAND predictions (801) and using a t-test analysis (802). For most value of false-positive rate DeMAND achieves a higher true-positive rate than a t-test. The straight line at the top-right for the DeMAND predictions indicates a random rank assignment for genes that are not in the regulatory network.

FIG. 8C shows, for the purpose of illustration and not limitation, the average true-positive rate (sensitivity) of known direct targets for all the compounds in the GEODB dataset using DeMAND (803) and using a t-test analysis (804), as a function of the number of top predictions. DeMAND outperforms the t-test analysis for a number of top genes and achieves almost 15% sensitivity in the top 100 predictions, while t-test achieves only 2% sensitivity.

Figure 9:
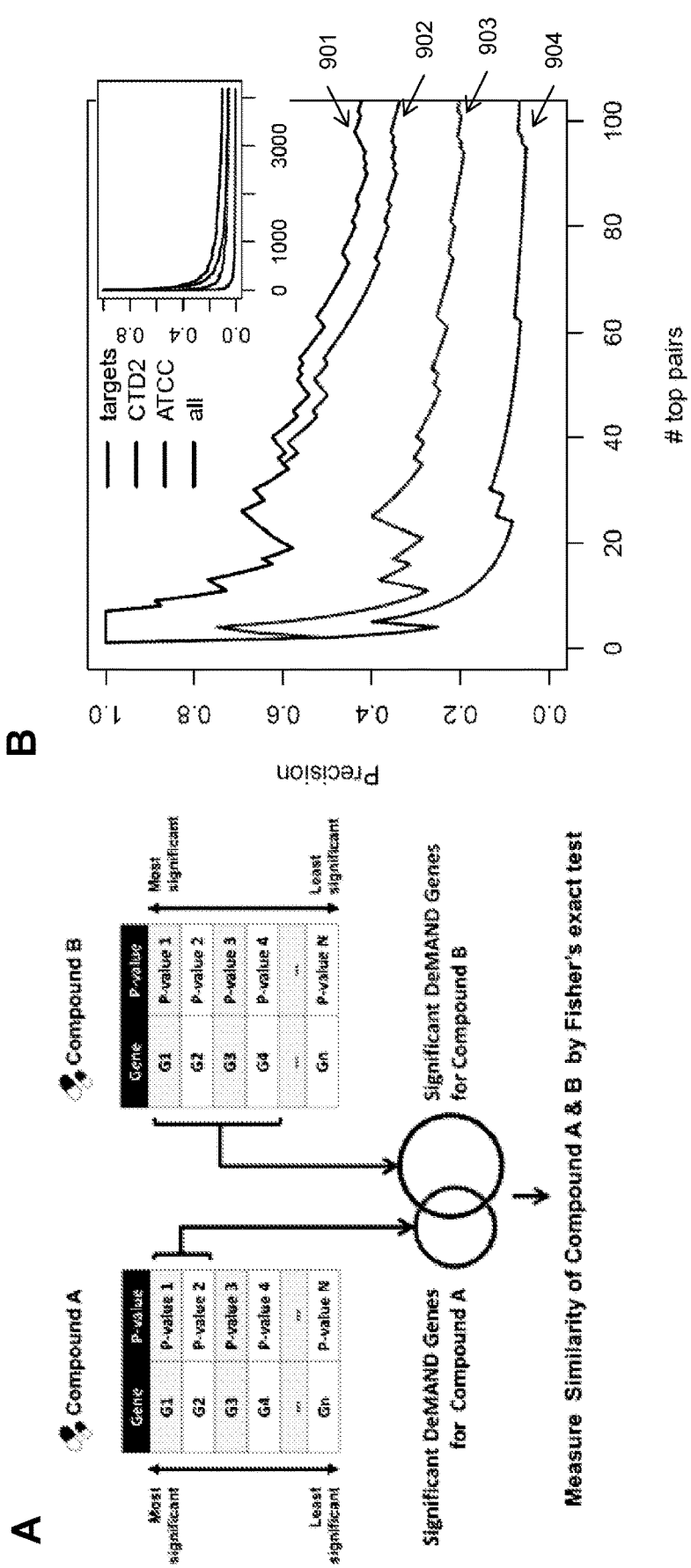
FIG. 9 illustrates an example prediction to detect compound similarities.

Referring to FIG. 9A for the purpose of illustration and not limitation, to detect similarities between compounds, DeMAND first infers the MoA of each compound. The similarity between the compound-pair is evaluated using the significance of the overlap between the lists by a Fisher exact test.

Referring to FIG. 9B for the purpose of illustration and not limitation, the rankings of the predicted similarities between the 92 compounds in the DP92 dataset is evaluated by the precision of each pair of compounds sharing known direct targets (903), producing a similar sensitivity profile according to the CTD2 data (904), sharing the same classification according to the Anatomical Therapeutic Chemical (ATC) Classification (902), or the above evidences (901). The results show that the predicted similarity is successful in discriminating compounds with similar MoA.

Referring to FIG. 10A for the purpose of illustration and not limitation, DeMAND-predicted compound pair similarities are enriched with compound-pairs with supporting external evidence. The compound pairs were sorted according to the significance of the overlap of their significant DeMAND predictions (by Fisher exact test), and the set of pairs with external evidence consists of compound pairs that share the same ATC class, or share established direct targets, or show a significant correlation using the $CTD^2$ data.

FIG. 10B shows, for the purpose of illustration and not limitation, the precision (true-positive rate) as a function of the sensitivity, where the positives are determined by pairs sharing the same direct target, or sharing the same ATC classification, or sharing a similar sensitivity profile across multiple cell lines according to the $CTD^2$ dataset. The curves are for compound similarities as predicted by overlap of significant DeMAND predictions (1001), overlap of significant genes by t-test analysis (1003), and similarity as calculated by the MANTRA algorithm (1002). T-test analysis achieves the worse precision, and DeMAND achieves the best precision for most values of sensitivity. Note that the t-test line ends short (at sensitivity of 0.14) since many compound pairs had no overlap of significantly differentially expressed genes.

FIG. 10C shows, for the purpose of illustration and not limitation, a comparison between the compound similarity in the $CTD^2$ dataset and the compound similarity as estimated by the overlap of significant DeMAND predictions. DeMAND similarity predictions provide a significant Spearman correlation of 0.59 (p-value=$7.8 \times 10^{-5}$) with the $CTD^2$ results.

FIG. 10D shows, for the purpose of illustration and not limitation, a comparison between the compound similarity in the $CTD^2$ dataset and the compound similarity as estimated by the MANTRA algorithm. MANTRA similarity predictions provide a non-significant Spearman correlation of 0.26 (p-value=0.11) with the $CTD^2$ results.

FIG. 10E shows, for the purpose of illustration and not limitation, a comparison between the compound similarity in the $CTD^2$ dataset and the compound similarity as estimated by the overlap of significantly differentially expressed by t-test. T-test similarity predictions provide a marginally significant Spearman correlation of 0.39 (p-value=0.013) with the $CTD^2$ results. It should be noted that multiple compounds had no overlap, and were therefore all ranked identically.

FIG. 11A shows, for the purpose of illustration and not limitation, GSH concentration following treatment of cells by negative control (DMSO, 1101), a positive control, sulfasalazine (1102), and by altretamine (1103) show that sulfasalazine treatment reduces the levels of active GSH compared to control, while altretamine treatment results in levels of active GSH that are indistinguishable from the control.

FIG. 11B shows, for the purpose of illustration and not limitation, the levels of a GPX4-specific substrate PC—OOH as measured by mass spectrometry of without cell lysate (1104), with untreated cell lysate (1105), and cell lysate from cells treated with altretamine (1106). When the cells are treated with altretamine the levels of PC—OOH are similar to no-lysate, and markedly different from the untreated lysate, indicating that altretamine treatment decreases the activity of GPX4.

FIG. 11C shows, for the purpose of illustration and not limitation, the levels of lipid reactive oxidative species (ROS) were measured by flow cytometry for control DMSO treated cells (1107), or following compound treatment (1108). Treatment by both compounds significantly increases the levels of lipid-ROS, exemplifying that the functional effect of altretamine treatment is similar to that of sulfasalazine.

Referring to FIG. 11D for the purpose of illustration and not limitation, sulfasalazine is known to act through System $x_c^-$ cystine/glutamate antiporter, causing a downstream effect on Glutathione (GSH) and GPX4, and leading to the accumulation of lipid reactive oxidative species. DeMAND predicted significant similarity between sulfasalazine and altretamine, but did not predict dysregulation of GSH by altretamine, while predicting dysregulation of GPX4. This prediction is validated by the experimental results in panels (A)-(C).

Figure 12A:
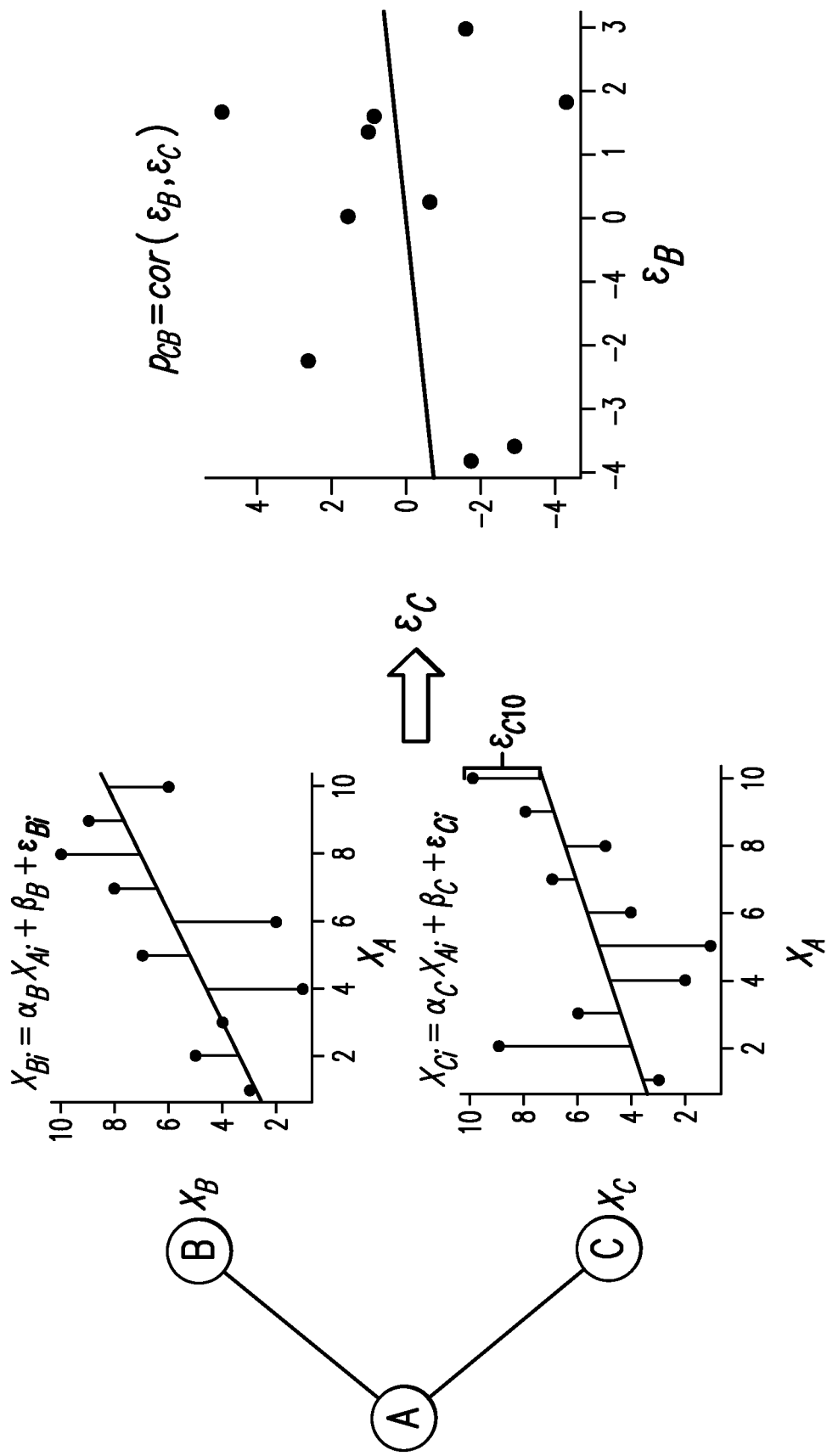
FIG. 12 illustrates estimating correlations between interactions and Brown's method correction of the p-values.

Referring to FIG. 12A for the purpose of illustration and not limitation, Brown's method of combining p-values requires estimating the correlations between the results that led to the p-values. To estimate the correlation between two interactions involving the same gene (A) the residuals from a linear fit for each gene interacting with A (genes B and C) is calculated, and the correlation between the residuals is calculated next.

Figure 12B:
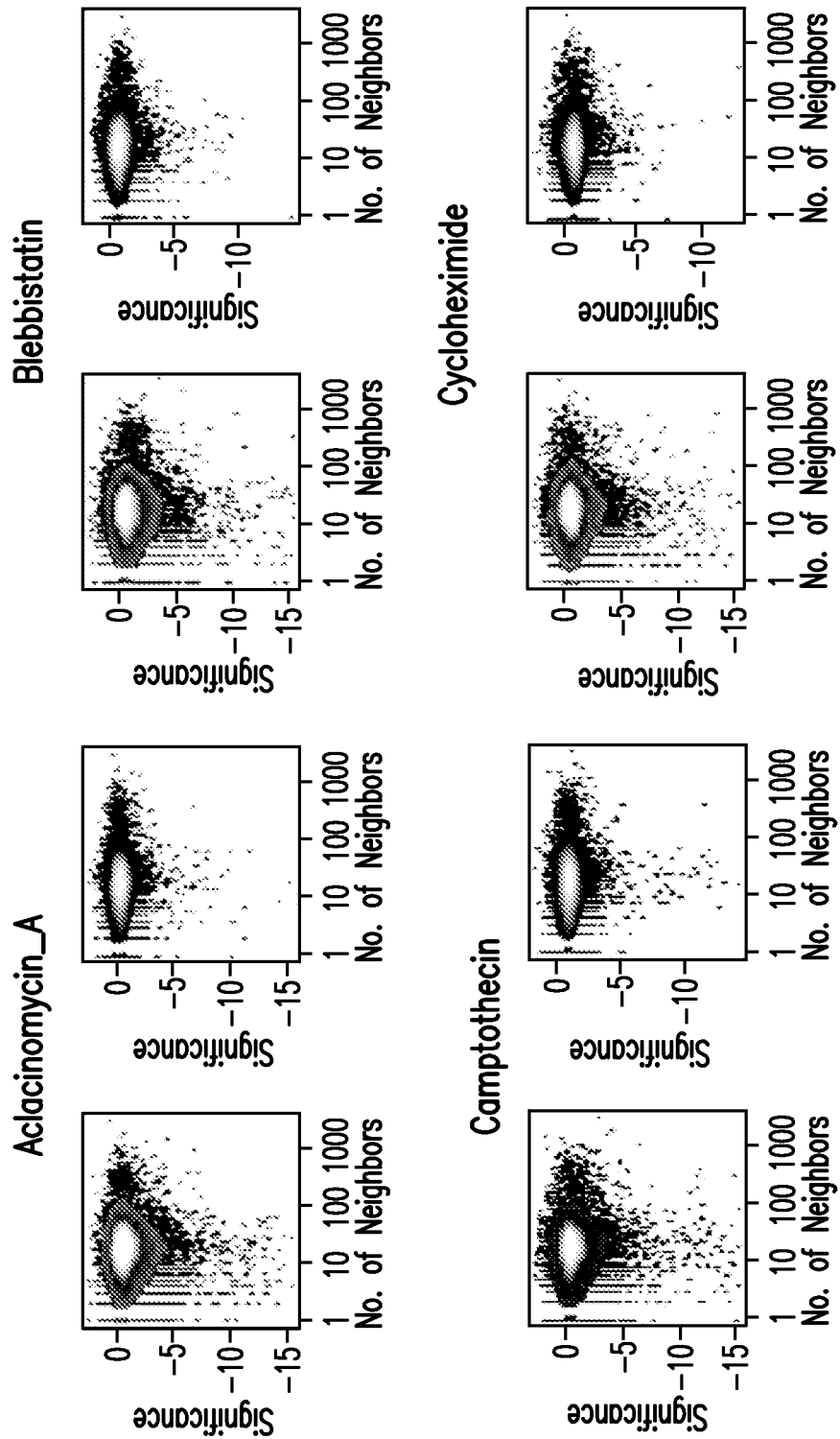
Figure 12B:
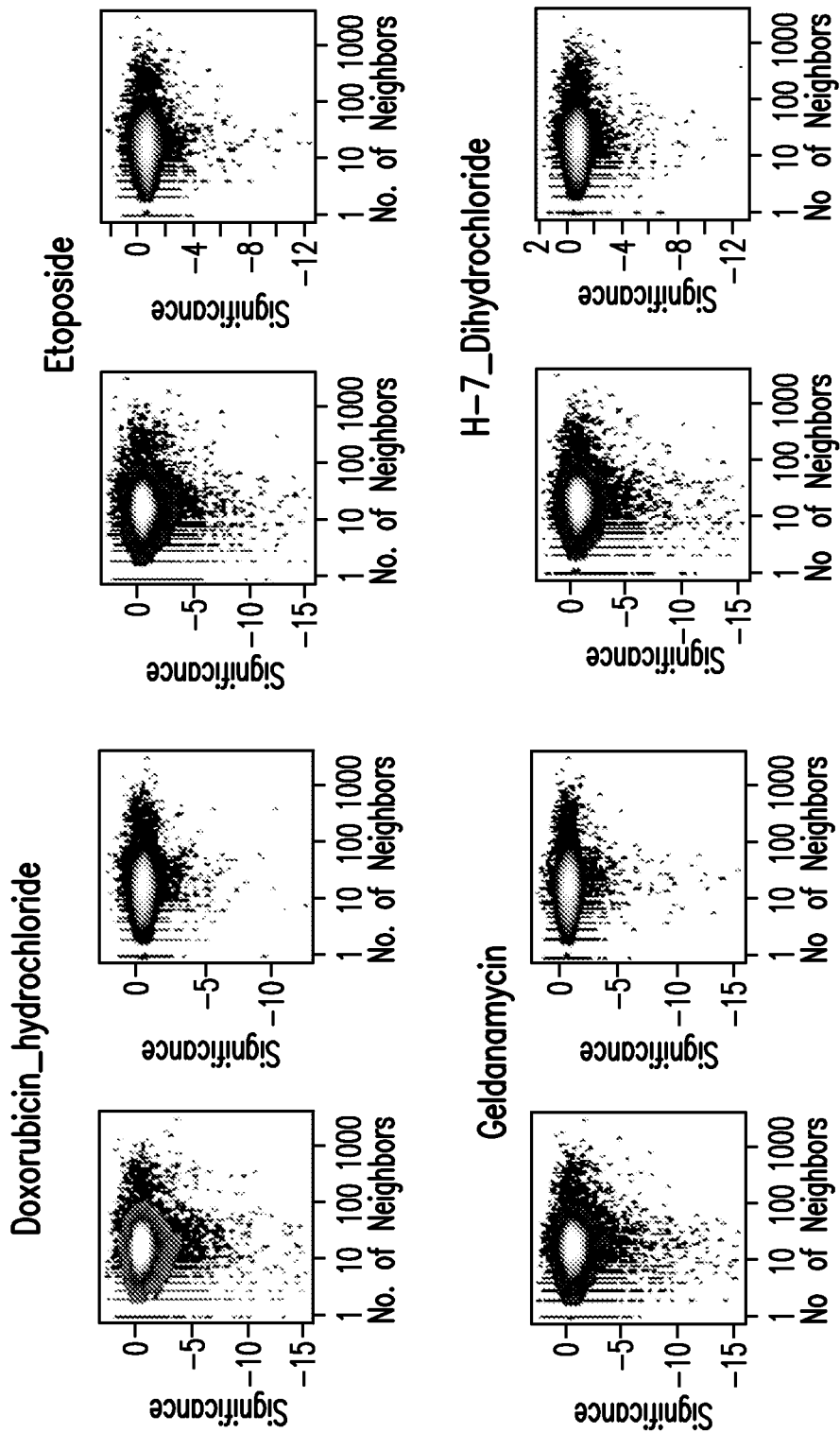
Figure 12B:
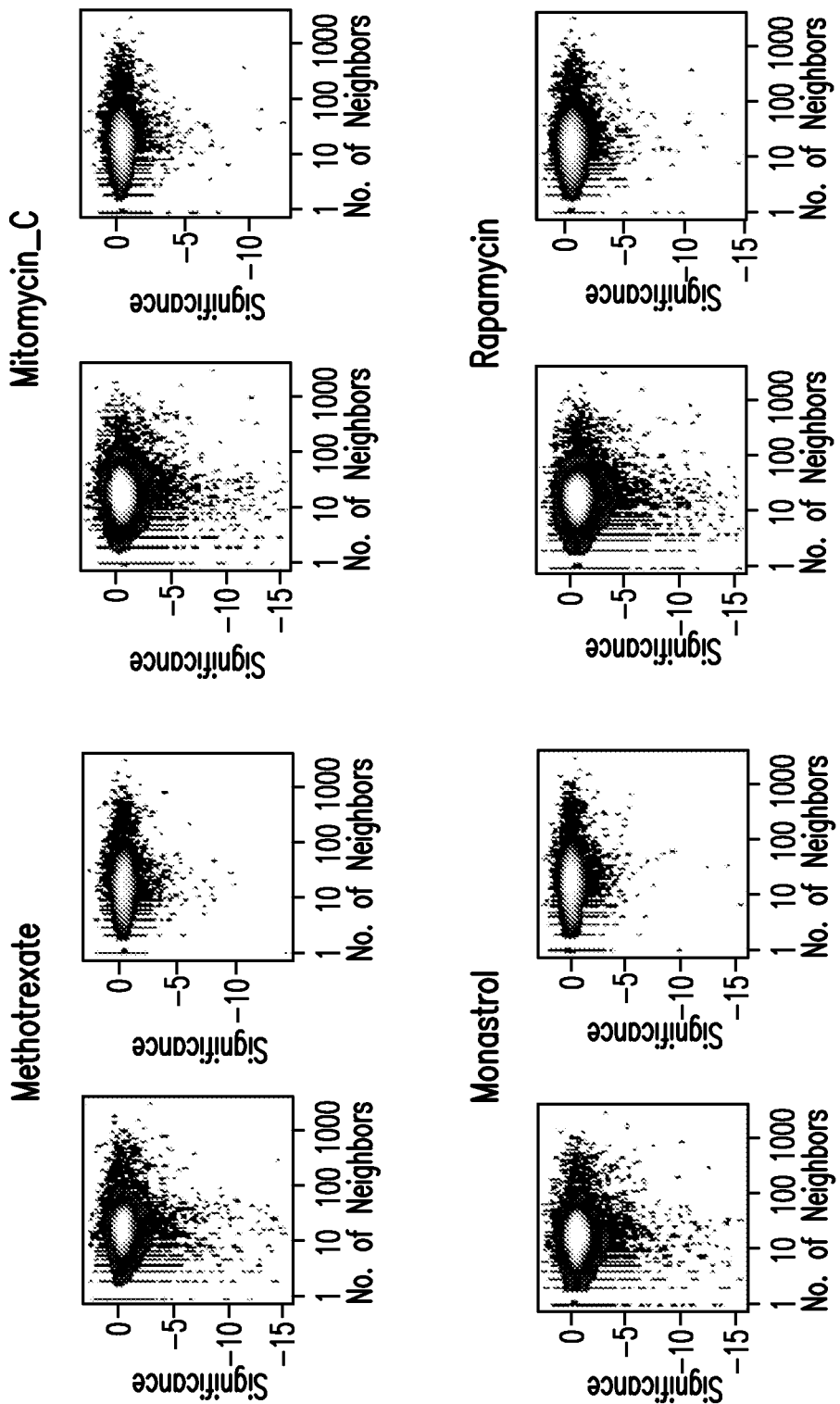
Figure 12B:
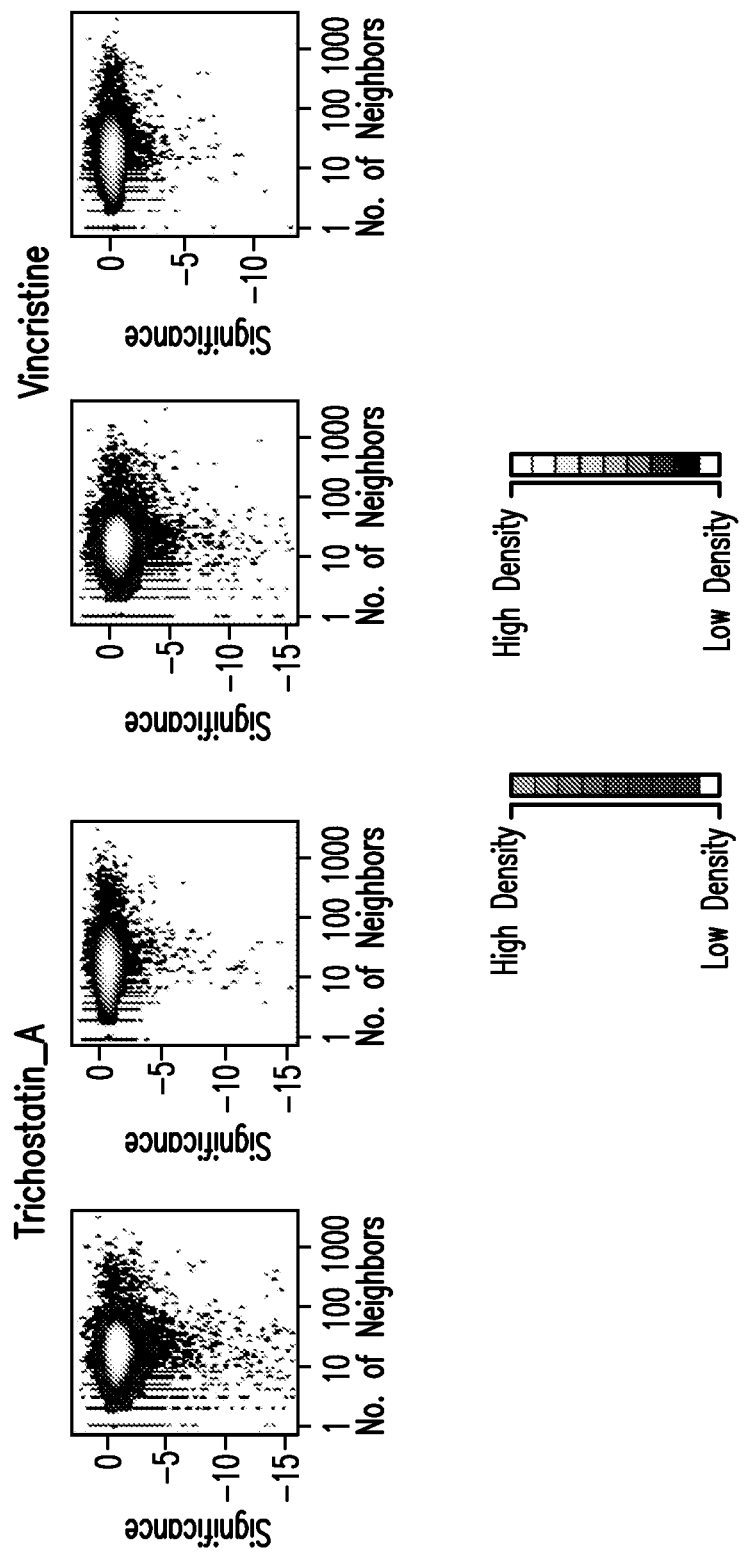

Referring to FIG. 12B for the purpose of illustration and not limitation, for the compounds in the DP14 dataset the probability density for the log 10 of the p-value for gene dysregulation is plotted as a function of the number of interactions the gene is involved in (degree). Before correction (left box) the probability distribution depends on the gene's degree, but after correction (right box) this bias is removed.

Experimental Procedures.

DeMAND can use as input a network, ε, and a gene expression set, GEP, separated into a control set $GEP^c$ and a perturbation set $GEP^p$. Each set contains measurements for N genes and $M_c$ and $M_p$ samples, respectively, giving a total of M samples.

The algorithm runs through each interaction $G_i \leftrightarrow G_j$ in the network (where $1 \leq i, j \leq N$), and estimates the joint probability distribution of obtaining the expression values $E_i$ and $E_j$ for genes $G_i$ and $G_j$, respectively. To do this, first the expression values are rank-transformed followed by Gaussian kernel smoothing, in which each expression point ($E_{im}$, $E_{jm}$) for sample $1 \leq m \leq M$ is replaced with a 2-dimensional Gaussian around that point. The standard deviations $\sigma^i$ and $\sigma_j$ of the Gaussian are obtained by Silverman's rule of thumb, giving $\sigma \approx 1.06 \delta M^{-1/6}$, with $\hat{\sigma}$ being the standard deviation of the data. Two probability distributions are then created, one for the control samples and one for the perturbation samples by summing the Gaussians of their corresponding samples. The distribution is then sampled at each integer point (k, l), where $1 \leq (k, l) \leq M$, giving $$P_{ij}^c(k,l) \propto \Sigma_{m \in M_c} \mathcal{G}(k-E_{im}, l-E_{jm}, \sigma_i, \sigma_j) \quad (8)$$

$$P_{ij}^p(k,l) \propto \Sigma_{m \in M_p} \mathcal{G}(k-E_{i,m}, l-E_{jm}, \sigma_i, \sigma_j) \quad (9)$$

These discrete probability distributions are normalized to ensure that the sum over k and l are equal to one.

Given the two probability distributions, one for the control samples and one for the perturbation samples, Kullback-Leibler divergence (KLD) between them was calculated to evaluate the difference between two distributions. This can be interpreted as the loss of information when trying to use one probability distribution to approximate another. The KLD in this context takes the form $$KLD(P_{ij}^c \mid P_{ij}^p) = \sum_{k=1}^{M} \sum_{l=1}^{M} P_{ij}^c(k,l) \log\left(\frac{p_{ij}^c(k,l)}{p_{ij}^p(k,l)}\right) \quad (10)$$

To ensure the symmetry of the distance the following equation was calculated $$KLD(P_{ij}^c, P_{ij}^p) = \frac{KLD(P_{ij}^c \mid P_{ij}^p) + KLD(p_{ij}^p \mid p_{ij}^c)}{2} \quad (11)$$

This can provide a measure of dysregulation for each edge in the network.

The null hypothesis is that the edge comprises of two genes whose interaction is not affected by the perturbation. Therefore, to create a distribution holding the expected values of such a hypothesis (also known as a null distribution), two genes were chosen at random and their KLD calculated. Note that the two genes in general do not share a network edge, and therefore there is no relationship between the levels of their expressions. Thus, a change in this association between observed using control and perturbation samples change, measured by the change in their probability distributions, should be thereby by chance.

This process is repeated $10^5$ times thereby creating a null model, which is then used to estimate the probability of obtaining a given value of KLD (or higher). This is done by counting the number of times such a value or higher was obtained in the null distribution and dividing it by the total number of values in the null. This is known as the p-value of the KLD, denoted $Pv_{ij}$.

To evaluate the dysregulation of each gene $G_i$, the p-values of all the interactions in which it is involved are integrated. This is done using Fisher's method from integrating p-values, such that the p-values are log transformed and summed to create a chi-square statistic $$x^2 = \Sigma_{G_i \leftrightarrow G_j \in \varepsilon} -2 \log Pv_{ij} \quad (12)$$

The integrated p-value is obtained from a chi-square distribution with 2k degrees of freedom, where k is the number of interactions that were integrated.

Fisher's method to integrate multiple p-values requires that these p-values be obtained from the independent experiments. However, in case of networks, this is not true and multiple interactions with a common gene could be co-related. To correct for this bias a modification of Brown's method is used. Specifically, the variance of the chi-square is defined as $$\sigma^2(X^2) = 4k + \Sigma_{i=1}^{k} \Sigma_{j=i+1}^{k} \varphi(\rho_{ij}) \quad (13)$$

where $\rho_{ij}$ is the correlation between the residuals of gene i and gene j, and $$\varphi(\rho_{ij}) = \begin{cases} \rho_{ij}(3.25 + 0.75\rho_{ij}) & 0 \leq \rho_{ij} \leq 1 \\ \rho_{ij}(3.27 + 0.71\rho_{ij}) & -0.5 \leq \rho_{ij} \leq 0 \end{cases} \quad (14)$$

Using this variance, the degrees of freedom are redefined to be $$df = \frac{8k^2}{\sigma^2(X^2)} \quad (15)$$

Note that here, the estimation of correlation between interactions is required and not between genes. To estimate the correlation between interactions $(G_i \leftrightarrow G_j)$ and $(G_i \leftrightarrow G_k)$, the residuals from a linear fit independently for genes $G_j$ and $G_k$ as a function of gene $G_i$ is estimated and used the correlation between these residuals as a surrogate for the correlation between the interactions. This is under the assumption that if two interactions are independent, then the residuals should not be correlated and a correlation between the residuals is due to the fact that these two interactions have a common gene. The resulting p-value is used as an estimate of the significance of the dysregulated of gene $G_i$.

In order to build tissue specific interactomes a Bayesian Evidence Integration Approach (BEIA) can be used. The Naïve Bayes Classification establishes that the probability of a specific interaction can be computed using the prior probability of that class of interactions and the product of the Likelihood Ratio (LR) of each clue supporting it. This approach requires large datasets of both positive and negative examples called Gold Standard Positive and Negative sets (GSP and GSN respectively) for both Protein-Protein Interactions (PPIs) and Protein-DNA Interactions (PDIs) to train each one of the clues. As required for the Naïve Bayes classifier, each of these evidence sources can be previously assessed to be independent from the rest.

In order to predict PPIs, the following evidence sources can be integrated.

Molecular interactions from the databases IntAct, BIND and MIPS for four eukaryotic organisms Human high-throughput screens The GeneWays literature data-mining algorithm The Gene Ontology 7 (GO) biological process annotations and Interpro protein domain annotations Likewise, co-expression data from a collection of GEPs from relevant tissue types can introduce the context specificity in each interactome.

The GSP for PPIs is a compendium from HPRD, BIND and IntAct databases containing a set of 48,648 unique PPIs involving 9,839 genes (after homodimers removal). The set of negative interactions GSN was defined as gene pairs from genes present in the GSP encoding proteins in distinct cell compartment representing a set of 5,362,594 negative gene pairs. It was previously estimated that there are ≈300,000 PPI interaction between the ≈22,000 genes in the genome, which means that 1 in 800 potential interactions occur. As a result, interactions with the likelihood ratio greater than 800 indicates 50% probability for it to be true positive.

In order to predict PDIs, the following evidence sources can be collected:

Mouse interactions from the TRANSFAC

BIND databases

TF binding sites (TFBS) identified in the promoter of target genes

The GeneWays literature data-mining algorithm

PDIs inferred from GEPs in each tissue type by the ARACNe algorithm can introduce the context specific information.

To generate the GSP for PDIs, human interactions were extracted from the Transfac® Professional (TRANSFAC), BIND and Myc (MycDB) databases. This resulted in a GSP PDI set of 4500 interactions involving 585 TFs and 2034 targets. The GSN was randomly generated containing 100,000 gene pairs composed of a TF and a target, excluding pairs where the two genes are involved in a GSP interaction or in the same biological process as defined by Gene Ontology.

The threshold for PDI was defined for each TF based on the number of targets for that TF in the ARACNe network. For example, the prior for a TF with 100 targets predicted by ARACNe among ≈22,000 potential targets will be 100/22000, which would indicate a LR>220. However, if the resulting cutoff was smaller than 5 (meaning that this TF regulates more than 5th of the genes) then LR>5 was used regardless.

Also, the reported interactomes also incorporate interacting pairs from both GSP involving genes expressed in each cellular context.

The foregoing merely illustrates the principles of the disclosed subject matter. Various modification and alterations to the described embodiments will be apparent to those skilled in the art in view of the teachings herein. It will thus be appreciated that those skilled in the art will be able to devise numerous techniques which, although not explicitly described herein, embody the principles of the disclosed subject matter and are thus within the spirit and scope.

The invention claimed is:

1. A method to identify a mechanism of action of a compound using network dysregulation using gene expression data acquired from both control and compound-perturbed states of a tissue-specific regulatory network, comprising:
   (a) selecting a tissue-specific regulatory network having a plurality of molecular interactions each connecting a pair of genes;
   (b) determining, using a processor, a two-dimensional probability density of gene expression levels for each of the interactions in a control state of the regulatory network;
   (c) determining, using the processor, a two-dimensional probability density of gene expression levels for each of the interactions in at least one compound-perturbed state of the regulatory network;
   (d) estimating, for each of the interactions, differences between the control probability density and the compound-perturbed probability density;
   (e) determining, where the estimated differences are statistically significant, a set of statistically significant dysregulated interactions, based only on the gene expression data;
   (f) ranking the statistically significant dysregulated interactions, to provide a set of candidate mechanism of action (MoA) genes; and
   (g) validating the MoA by confirming, in a tissue having the tissue-specific regulatory network, a direct primary target interaction and/or an indirect effector interaction between the compound and the candidate MoA genes.

2. The method of claim 1, wherein the estimating comprises estimating on an interaction by interaction basis.

3. The method of claim 1, wherein the estimating comprises using a Kullback-Leibler divergence.

4. The method of claim 3, wherein determining whether the estimated changes are statistically significant further comprises using a null distribution generated by $10^5$ Kullback-Leibler values estimated from random pairs of genes, and providing a P-value for the dysregulation of each edge in the network.

5. The method of claim 1, wherein the interactions comprise every interaction ending in at least a first gene in the regulatory network.

6. The method of claim 5, comprising determining whether the first gene is dysregulated based at least in part on the significance of each interaction.

7. The method of claim 6, wherein the at least a first gene comprises a plurality of genes, and further comprising determining whether each of the plurality of genes is dysregulated.

8. The method of claim 5, wherein the at least one compound comprises a plurality of compounds, further comprising repeating (a)-(g) for each of the plurality of compounds, and identifying two or more compounds with similar MoA.

9. A method to identify compounds with similar pharmacological effect using gene expression data acquired from both control and compound-perturbed states of a tissue-specific regulatory network, comprising:
   (a) selecting a tissue-specific regulatory network having a plurality of molecular interactions each connecting a pair of genes, and having a first interaction involving at least a first gene;
   (b) determining, using a processor, a first n-dimensional probability density of gene expression levels for the first gene and one or more genes in a control state of the regulatory network;
   (c) determining, using the processor, a second n-dimensional probability density of gene expression levels for the first gene and the one or more genes in a first compound-perturbed state of the regulatory network;
   (d) estimating changes between the first probability density and the second probability density;
   (e) determining that the estimated changes are statistically significant,
   (f) determining, where the estimated changes are statistically significant, that the interaction is dysregulated;
   (g) repeating (a)-(f) for each of m interactions wherein the m interactions comprise every interaction ending in the first gene in the regulatory network;
   (h) determining whether the first gene is dysregulated based at least in part on the significance of each interaction;
   (i) repeating (a)-(h) for a plurality of genes;
   (j) identifying a mechanism of action (MoA) of the first compound by selecting genes that are dysregulated, based only on the gene expression data;
   (k) validating the MoA by confirming, in a tissue having the tissue-specific regulatory network, a direct primary target interaction and/or an indirect effector interaction between the compound and the candidate MoA genes;
   (l) repeating (a)-(j) for a plurality of compound treatments using a plurality of compounds; and (m) identifying two or more compounds with similar pharmacological effect, based on similar MoA.

10. The method of claim 9, wherein the estimating comprises estimating on an interaction by interaction basis.

11. The method of claim 9, wherein the estimating comprises using a Kullback-Leibler divergence.

* * * * *

```
                        SEQUENCE LISTING

<160> NUMBER OF SEQ ID NOS: 20

<210> SEQ ID NO 1
<211> LENGTH: 19
<212> TYPE: RNA
<213> ORGANISM: Artificial Sequence
<220> FEATURE:
<223> OTHER INFORMATION: CCNB1 siRNA

<400> SEQUENCE: 1
caacauuacc ugucauaua                                                    19

<210> SEQ ID NO 2
<211> LENGTH: 19
<212> TYPE: RNA
<213> ORGANISM: Artificial Sequence
<220> FEATURE:
<223> OTHER INFORMATION: CCNB1 siRNA

<400> SEQUENCE: 2
ugcacuaguu caagauuua                                                    19

<210> SEQ ID NO 3
<211> LENGTH: 19
<212> TYPE: RNA
<213> ORGANISM: Artificial Sequence
<220> FEATURE:
<223> OTHER INFORMATION: CCNB1 siRNA

<400> SEQUENCE: 3
gaauguaguc augguaaau                                                    19

<210> SEQ ID NO 4
<211> LENGTH: 19
<212> TYPE: RNA
<213> ORGANISM: Artificial Sequence
<220> FEATURE:
<223> OTHER INFORMATION: CCNB1 siRNA

<400> SEQUENCE: 4
cuaauugacu ggcuaguac                                                    19

<210> SEQ ID NO 5
<211> LENGTH: 19
<212> TYPE: RNA
<213> ORGANISM: Artificial Sequence
<220> FEATURE:
<223> OTHER INFORMATION: RPS3A siRNA

<400> SEQUENCE: 5
ggcaagaaca agcgccuua                                                    19

<210> SEQ ID NO 6
<211> LENGTH: 19
```

<212> TYPE: RNA
<213> ORGANISM: Artificial Sequence
<220> FEATURE:
<223> OTHER INFORMATION: RPS3A siRNA

<400> SEQUENCE: 6
gcaacaauca gauacggaa                                                    19

<210> SEQ ID NO 7
<211> LENGTH: 19
<212> TYPE: RNA
<213> ORGANISM: Artificial Sequence
<220> FEATURE:
<223> OTHER INFORMATION: RPS3A siRNA

<400> SEQUENCE: 7
gauugaagcu cacguugau                                                    19

<210> SEQ ID NO 8
<211> LENGTH: 19
<212> TYPE: RNA
<213> ORGANISM: Artificial Sequence
<220> FEATURE:
<223> OTHER INFORMATION: RPS3A siRNA

<400> SEQUENCE: 8
ucaagacuac cgaugguua                                                    19

<210> SEQ ID NO 9
<211> LENGTH: 19
<212> TYPE: RNA
<213> ORGANISM: Artificial Sequence
<220> FEATURE:
<223> OTHER INFORMATION: VHL siRNA

<400> SEQUENCE: 9
aggcaggcgu cgaagagua                                                    19

<210> SEQ ID NO 10
<211> LENGTH: 19
<212> TYPE: RNA
<213> ORGANISM: Artificial Sequence
<220> FEATURE:
<223> OTHER INFORMATION: VHL siRNA

<400> SEQUENCE: 10
ccacccaaau gugcagaaa                                                    19

<210> SEQ ID NO 11
<211> LENGTH: 19
<212> TYPE: RNA
<213> ORGANISM: Artificial Sequence
<220> FEATURE:
<223> OTHER INFORMATION: VHL siRNA

<400> SEQUENCE: 11
ggagcgcauu gcacaucaa                                                    19

<210> SEQ ID NO 12
<211> LENGTH: 19
<212> TYPE: RNA
<213> ORGANISM: Artificial Sequence
<220> FEATURE:
<223> OTHER INFORMATION: VHL siRNA

<400> SEQUENCE: 12

```
ccaauggauu cauggagua                                           19

<210> SEQ ID NO 13
<211> LENGTH: 19
<212> TYPE: RNA
<213> ORGANISM: Artificial Sequence
<220> FEATURE:
<223> OTHER INFORMATION: NFKBIA siRNA

<400> SEQUENCE: 13
agucagaguu cacggaguu                                           19

<210> SEQ ID NO 14
<211> LENGTH: 19
<212> TYPE: RNA
<213> ORGANISM: Artificial Sequence
<220> FEATURE:
<223> OTHER INFORMATION: NFKBIA siRNA

<400> SEQUENCE: 14
gcugauguca acagaguua                                           19

<210> SEQ ID NO 15
<211> LENGTH: 19
<212> TYPE: RNA
<213> ORGANISM: Artificial Sequence
<220> FEATURE:
<223> OTHER INFORMATION: NFKBIA siRNA

<400> SEQUENCE: 15
aggacgagcu gcccuauga                                           19

<210> SEQ ID NO 16
<211> LENGTH: 19
<212> TYPE: RNA
<213> ORGANISM: Artificial Sequence
<220> FEATURE:
<223> OTHER INFORMATION: NFKBIA siRNA

<400> SEQUENCE: 16
gugcugaugu caaugcuca                                           19

<210> SEQ ID NO 17
<211> LENGTH: 19
<212> TYPE: RNA
<213> ORGANISM: Artificial Sequence
<220> FEATURE:
<223> OTHER INFORMATION: TUBB siRNA

<400> SEQUENCE: 17
ggaaugggca cucuccuua                                           19

<210> SEQ ID NO 18
<211> LENGTH: 19
<212> TYPE: RNA
<213> ORGANISM: Artificial Sequence
<220> FEATURE:
<223> OTHER INFORMATION: TUBB siRNA

<400> SEQUENCE: 18
aagaauaccc ugaucgcau                                           19

<210> SEQ ID NO 19
<211> LENGTH: 19
<212> TYPE: RNA
<213> ORGANISM: Artificial Sequence
```

```
<220> FEATURE:
<223> OTHER INFORMATION: TUBB siRNA

<400> SEQUENCE: 19
uccaucaguu gguagagaa                                                    19

<210> SEQ ID NO 20
<211> LENGTH: 19
<212> TYPE: RNA
<213> ORGANISM: Artificial Sequence
<220> FEATURE:
<223> OTHER INFORMATION: TUBB siRNA

<400> SEQUENCE: 20
ccgcaucucu guguacuac                                                    19
```